US011338029B2

(12) United States Patent
Yan et al.

(10) Patent No.: US 11,338,029 B2
(45) Date of Patent: May 24, 2022

(54) CANCER VACCINES TARGETING PRAME AND USES THEREOF

(71) Applicant: Inovio Pharmaceuticals, Inc., Plymouth Meeting, PA (US)

(72) Inventors: Jian Yan, Wallingford, PA (US); Anna Slager, Lansdale, PA (US); Bradley Garman, Glenside, PA (US); Neil Cooch, Oreland, PA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 346 days.

(21) Appl. No.: 16/219,356

(22) Filed: Dec. 13, 2018

(65) Prior Publication Data

US 2019/0175713 A1 Jun. 13, 2019

Related U.S. Application Data

(60) Provisional application No. 62/598,290, filed on Dec. 13, 2017.

(51) Int. Cl.
| | | |
|---|---|---|
| *A61P 35/00* | (2006.01) | |
| *C12N 15/62* | (2006.01) | |
| *A61K 39/00* | (2006.01) | |

(52) U.S. Cl.
CPC ...... *A61K 39/001189* (2018.08); *C12N 15/62* (2013.01); *A61K 2039/53* (2013.01); *A61K 2039/55527* (2013.01); *A61K 2039/55533* (2013.01); *A61K 2039/55538* (2013.01); *A61P 35/00* (2018.01)

(58) Field of Classification Search
CPC ........ A61K 39/001189; A61K 2039/53; A61P 35/00
USPC ...................................................... 424/277.1
See application file for complete search history.

(56) References Cited

U.S. PATENT DOCUMENTS

| 8,969,544 B2 | 3/2015 | Bernards et al. |
| 2016/0030536 A1 | 2/2016 | Weiner et al. |
| 2016/0333065 A1 | 11/2016 | Kessler et al. |

FOREIGN PATENT DOCUMENTS

| RU | 2273645 C2 | 4/2006 |
| RU | 2502800 C2 | 12/2013 |

OTHER PUBLICATIONS

International Search Report and Written Opinion issued in PCT/US18/65522, dated Apr. 1, 2019.
Baldueva, "Anti Tumor Vaccines", Practical Oncology, vol. 4, No. 3, 2003, pp. 157-166; retrieved from https://rosoncoweb.ru/library/journals/practical_oncology/arh015/05.pdf on Oct. 7, 2020 [with machine-generated translation].
Bullinger et al.; "PRAME—Induced Inhibition of Retinoic Acid Receptor Signaling-Mediated Differentiation—A Possible Target for ATRA Response in AML without t(15;17)"; Clinical Cancer Research; vol. 19; May 2013; p. 2562-2571.
European search report dated Aug. 31, 2021 for EP Application No. 18888094.
Weber et al.; "A Phase 1 Study of a Vaccine Targeting Preferentially Expressed Antigen in Melanoma and Prostate-specific Membrane Antigen in Patients with Advanced Solid Tumors"; Journal of Immunotherapy; vol. 34; Sep. 2011; p. 556-567.

*Primary Examiner* — Yan Xiao
(74) *Attorney, Agent, or Firm* — BakerHostetler

(57) ABSTRACT

Disclosed herein are nucleic acid molecules comprising one or more nucleic acid sequences that encode a mutated consensus PRAME antigen. Vectors, compositions, and vaccines comprising one or more nucleic acid sequences that encode a mutated consensus PRAME antigen are disclosed. Methods of treating a subject with a PRAME-expressing tumor and methods of preventing a PRAME-expressing tumor are disclosed. Mutated consensus PRAME antigen is disclosed.

19 Claims, 22 Drawing Sheets

Specification includes a Sequence Listing.

FIG. 2

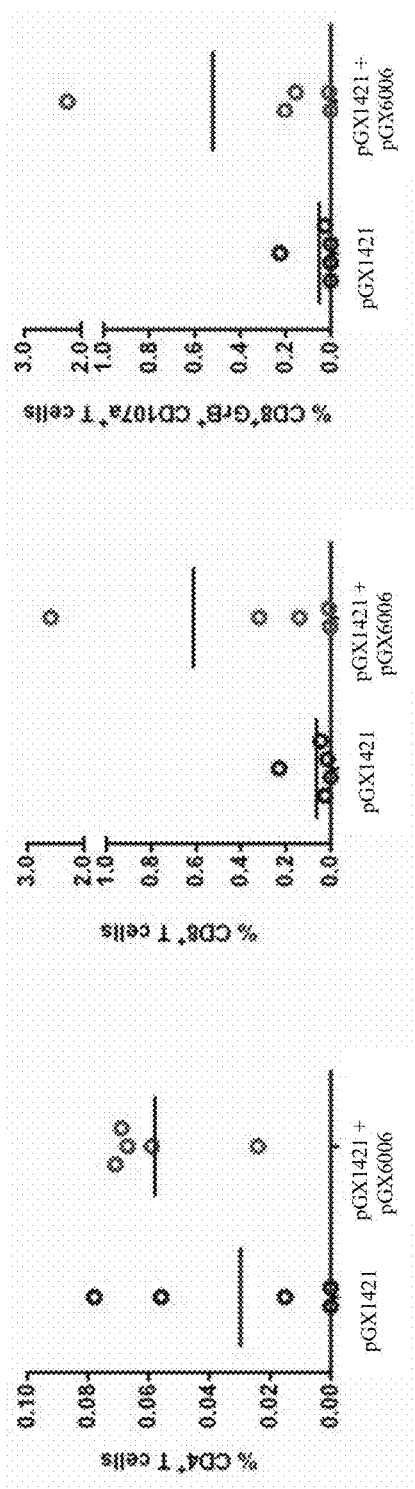
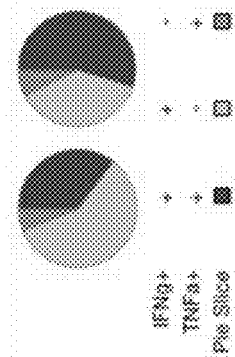
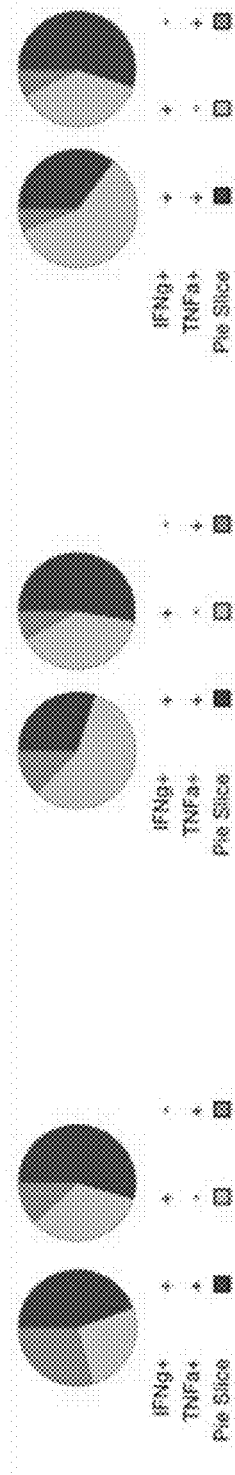
FIG. 17A  FIG. 17B  FIG. 17C
FIG. 17D  FIG. 17E  FIG. 17F

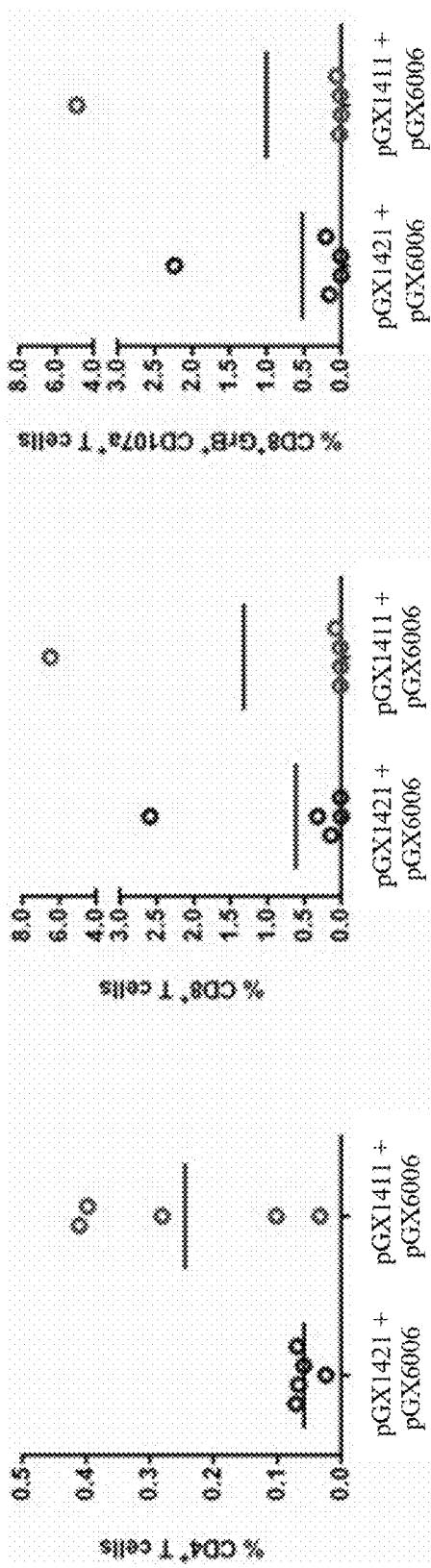
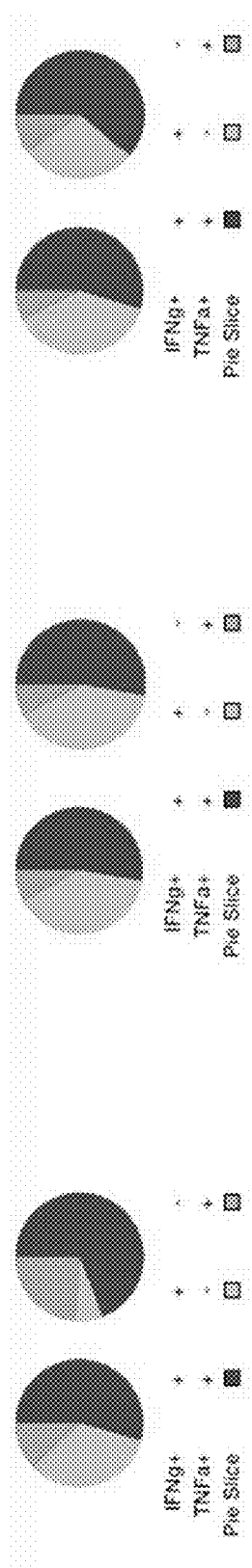
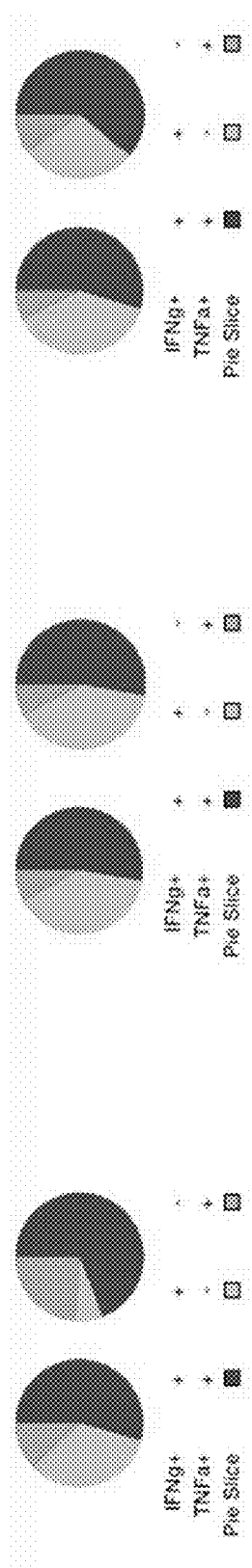
FIG. 19A  FIG. 19B  FIG. 19C
FIG. 19D  FIG. 19E  FIG. 19F

SEQUENCE LISTING

<160> NUMBER OF SEQ ID NOS: 74

<210> SEQ ID NO 1
<211> LENGTH: 1584
<212> TYPE: DNA
<213> ORGANISM: Artificial Sequence
<220> FEATURE:
<221> NAME/KEY: source
<223> OTHER INFORMATION: /note="Description of Artificial Sequence:
  Synthetic polynucleotide"
<220> FEATURE:
<221> NAME/KEY: source
<223> OTHER INFORMATION: /note="Synthetic Consensus PRAME DNA Coding
  Sequence pGX1421"

<400> SEQUENCE: 1
atggactgga catggattct gttcctggtc gctgctgcta cacgggtgca ttcagagaga    60
cgaagactgc gggctcaat tcagagtagg tacatcagta tgtcagtctg gacctcacca    120
cggagactgg tggaactggc cgggcagagc ctgctgaagg atgaggccct ggctattgcc    180
gctctggaac tgctgccccg agagctgttc cctcccctgt tcatggcagc cttcgacgga    240
cgccacagcc agactctgaa ggctatggtc caggcatggc ccttttacctg cctgcctctg    300 ggcgtgctga tgaaggggca gcagctgcat ctggagactt tcaaagcagt gctggatggc    360

```
ctggacgtgc tgctggccca ggaagtgagg cctaggcgct ggaagctgga ggtcctggat    420
ctgcgcaaaa acagccacca ggactttttgg accgtgtggt ccgggaatcg gccagtctg    480
tactcattcc cagaacccga ggctgcacag ccaatgcgga agaaaagaaa ggtggatgga    540
ctgtccaccg aagctgagca gccttttaca ccaatcgaag tgctggtcga tctgtccctg    600
aaagaaggcg catgcgacga gctgttctct tatctgatgg agaaggtcaa agacagaag    660
aacgtgctgc acctgtgctg taagaaactg aaaatctttg ctatgccat gcaggacatc    720
aagatgattc tgaaaatggt ccagctggat tccattgaag acctggaggt cacttgtacc    780
tggaagctgc aacactggcc aaattctct ccctacctgg acagatgat caatctgcga    840
cggctgctgc tgtctcacat ccatgctagc tcctctatta gtcctgagaa ggaggaagag    900
tacattgcac agtttacttc tcagttcctg agtctgcagt gcctgcaggc cctgtatgtg    960
gatagcctgt ctttctgag aggcaggctg gaccagctgc tgcgacacgt catgaacccc   1020
ctggaaacac tgagtgtgac taattgtaga ctgtcagagg gcgatgtgat gcatctgagc   1080
cagtcccta acgtgagcca gctgtccgtc ctgtctctga gtggcgtgat gctgacagac   1140
gtgagccctg aaccactgca ggccctgctg agcgagcat ctgccactct gcaggacctg   1200
gattttgacg agtgtgggat catggacgat cagctgctgg tgctgctgcc ttcactgagc   1260
cactgctccc agctgaccac actgtctttc tgtgggaacc caatctccat ttctgtgctg   1320
cagaatctgc tgcaccatct gattggactg agcaacctga cccatgtgct gtaccccgtc   1380
cctctggaaa gctatgagga tgtgcacgga acactgcatc tgggcaggct ggcctatctg   1440
cacgctcgcc tgcgagaagt ggtgtgcgag ctgggcagac cctcaatggt gtggctgagc   1500
gccaatccat gtccccattg cggcgaccgg acattctacg accccgaacc tattctgtgc   1560
ccctgcttca tgcctaactg ataa                                          1584
```

<210> SEQ ID NO 2
<211> LENGTH: 526
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Synthetic Consensus PRAME Protein Coding Sequence pGX1421"

<400> SEQUENCE: 2

Met Asp Trp Thr Trp Ile Leu Phe Leu Val Ala Ala Ala Thr Arg Val
1               5                   10                  15

His Ser Glu Arg Arg Leu Arg Gly Ser Ile Gln Ser Arg Tyr Ile
            20                  25                  30

Ser Met Ser Val Trp Thr Ser Pro Arg Arg Leu Val Glu Leu Ala Gly
        35                  40                  45

Gln Ser Leu Leu Lys Asp Glu Ala Leu Ala Ile Ala Ala Leu Glu Leu
    50                  55                  60

Leu Pro Arg Glu Leu Phe Pro Pro Leu Phe Met Ala Ala Phe Asp Gly
65                  70                  75                  80

Arg His Ser Gln Thr Leu Lys Ala Met Val Gln Ala Trp Pro Phe Thr
                85                  90                  95

Cys Leu Pro Leu Gly Val Leu Met Lys Gly Gln Gln Leu His Leu Glu
            100                 105                 110

-continued

```
Thr Phe Lys Ala Val Leu Asp Gly Leu Asp Val Leu Ala Gln Glu
    115                 120                 125
Val Arg Pro Arg Arg Trp Lys Leu Glu Val Leu Asp Leu Arg Lys Asn
130                 135                 140
Ser His Gln Asp Phe Trp Thr Val Trp Ser Gly Asn Arg Ala Ser Leu
145                 150                 155                 160
Tyr Ser Phe Pro Glu Pro Glu Ala Ala Gln Pro Met Arg Lys Lys Arg
                165                 170                 175
Lys Val Asp Gly Leu Ser Thr Glu Ala Glu Gln Pro Phe Thr Pro Ile
                180                 185                 190
Glu Val Leu Val Asp Leu Ser Leu Lys Glu Gly Ala Cys Asp Glu Leu
            195                 200                 205
Phe Ser Tyr Leu Met Glu Lys Val Lys Arg Gln Lys Asn Val Leu His
210                 215                 220
Leu Cys Cys Lys Lys Leu Lys Ile Phe Ala Met Pro Met Gln Asp Ile
225                 230                 235                 240
Lys Met Ile Leu Lys Met Val Gln Leu Asp Ser Ile Glu Asp Leu Glu
                245                 250                 255
Val Thr Cys Thr Trp Lys Leu Pro Thr Leu Ala Lys Phe Ser Pro Tyr
            260                 265                 270
Leu Gly Gln Met Ile Asn Leu Arg Arg Leu Leu Leu Ser His Ile His
            275                 280                 285
Ala Ser Ser Ser Ile Ser Pro Glu Lys Glu Glu Tyr Ile Ala Gln
            290                 295                 300
Phe Thr Ser Gln Phe Leu Ser Leu Gln Cys Leu Gln Ala Leu Tyr Val
305                 310                 315                 320
Asp Ser Leu Phe Phe Leu Arg Gly Arg Leu Asp Gln Leu Leu Arg His
                325                 330                 335
Val Met Asn Pro Leu Glu Thr Leu Ser Val Thr Asn Cys Arg Leu Ser
            340                 345                 350
Glu Gly Asp Val Met His Leu Ser Gln Ser Pro Asn Val Ser Gln Leu
            355                 360                 365
Ser Val Leu Ser Leu Ser Gly Val Met Leu Thr Asp Val Ser Pro Glu
370                 375                 380
Pro Leu Gln Ala Leu Leu Glu Arg Ala Ser Ala Thr Leu Gln Asp Leu
385                 390                 395                 400
Asp Phe Asp Glu Cys Gly Ile Met Asp Asp Gln Leu Leu Val Leu Leu
                405                 410                 415
Pro Ser Leu Ser His Cys Ser Gln Leu Thr Thr Leu Ser Phe Cys Gly
            420                 425                 430
Asn Pro Ile Ser Ile Ser Val Leu Gln Asn Leu Leu His His Leu Ile
            435                 440                 445
Gly Leu Ser Asn Leu Thr His Val Leu Tyr Pro Val Pro Leu Glu Ser
450                 455                 460
Tyr Glu Asp Val His Gly Thr Leu His Leu Gly Arg Leu Ala Tyr Leu
465                 470                 475                 480
His Ala Arg Leu Arg Glu Val Val Cys Glu Leu Gly Arg Pro Ser Met
                485                 490                 495
Val Trp Leu Ser Ala Asn Pro Cys Pro His Cys Gly Asp Arg Thr Phe
            500                 505                 510
Tyr Asp Pro Glu Pro Ile Leu Cys Pro Cys Phe Met Pro Asn
            515                 520                 525
```

```
<210> SEQ ID NO 3
<211> LENGTH: 5
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any amino acid

<400> SEQUENCE: 3

Leu Xaa Xaa Leu Leu
1               5

<210> SEQ ID NO 4
<211> LENGTH: 5
<212> TYPE: PRT
<213> ORGANISM: Homo sapiens

<400> SEQUENCE: 4

Leu Arg Glu Leu Leu
1               5

<210> SEQ ID NO 5
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Arg Val His Ser Glu Arg Arg Leu Arg Gly Ser Ile Gln Ser
1               5                   10                  15

<210> SEQ ID NO 6
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Arg Leu Arg Gly Ser Ile Gln Ser Arg Tyr Ile Ser Met Ser Val
1               5                   10                  15

<210> SEQ ID NO 7
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Ser Arg Tyr Ile Ser Met Ser Val Trp Thr Ser Pro Arg Arg Leu
1               5                   10                  15

<210> SEQ ID NO 8
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
```

```
<400> SEQUENCE: 8

Val Trp Thr Ser Pro Arg Arg Leu Val Glu Leu Ala Gly Gln Ser
1               5                   10                  15

<210> SEQ ID NO 9
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Leu Val Glu Leu Ala Gly Gln Ser Leu Leu Lys Asp Glu Ala Leu
1               5                   10                  15

<210> SEQ ID NO 10
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ser Leu Leu Lys Asp Glu Ala Leu Ala Ile Ala Ala Leu Glu Leu
1               5                   10                  15

<210> SEQ ID NO 11
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Leu Leu Pro Arg Glu Leu Phe Pro Pro Leu Phe Met Ala Ala Phe
1               5                   10                  15

<210> SEQ ID NO 12
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Pro Pro Leu Phe Met Ala Ala Phe Asp Gly Arg His Ser Gln Thr
1               5                   10                  15

<210> SEQ ID NO 13
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13
```

```
Phe Asp Gly Arg His Ser Gln Thr Leu Lys Ala Met Val Gln Ala
1               5                   10                  15
```

<210> SEQ ID NO 14
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

```
Thr Leu Lys Ala Met Val Gln Ala Trp Pro Phe Thr Cys Leu Pro
1               5                   10                  15
```

<210> SEQ ID NO 15
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

```
Ala Trp Pro Phe Thr Cys Leu Pro Leu Gly Val Leu Met Lys Gly
1               5                   10                  15
```

<210> SEQ ID NO 16
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

```
Pro Leu Gly Val Leu Met Lys Gly Gln Gln Leu His Leu Glu Thr
1               5                   10                  15
```

<210> SEQ ID NO 17
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

```
Gly Gln Gln Leu His Leu Glu Thr Phe Lys Ala Val Leu Asp Gly
1               5                   10                  15
```

<210> SEQ ID NO 18
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

```
Thr Phe Lys Ala Val Leu Asp Gly Leu Asp Val Leu Leu Ala Gln
1               5                   10                  15
```

-continued

```
<210> SEQ ID NO 19
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly Leu Asp Val Leu Leu Ala Gln Glu Val Arg Pro Arg Arg Trp
1               5                   10                  15

<210> SEQ ID NO 20
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gln Glu Val Arg Pro Arg Arg Trp Lys Leu Glu Val Leu Asp Leu
1               5                   10                  15

<210> SEQ ID NO 21
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Trp Lys Leu Glu Val Leu Asp Leu Arg Lys Asn Ser His Gln Asp
1               5                   10                  15

<210> SEQ ID NO 22
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Leu Arg Lys Asn Ser His Gln Asp Phe Trp Thr Val Trp Ser Gly
1               5                   10                  15

<210> SEQ ID NO 23
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Phe Trp Thr Val Trp Ser Gly Asn Arg Ala Ser Leu Tyr Ser
1               5                   10                  15

<210> SEQ ID NO 24
<211> LENGTH: 15
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 24

Gly Asn Arg Ala Ser Leu Tyr Ser Phe Pro Glu Pro Glu Ala Ala
1               5                   10                  15

<210> SEQ ID NO 25
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ser Phe Pro Glu Pro Glu Ala Ala Gln Pro Met Arg Lys Lys Arg
1               5                   10                  15

<210> SEQ ID NO 26
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ala Gln Pro Met Arg Lys Lys Arg Lys Val Asp Gly Leu Ser Thr
1               5                   10                  15

<210> SEQ ID NO 27
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Arg Lys Val Asp Gly Leu Ser Thr Glu Ala Glu Gln Pro Phe Thr
1               5                   10                  15

<210> SEQ ID NO 28
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Thr Pro Ile Glu Val Leu Val Asp Leu Ser Leu Lys Glu Gly Ala
1               5                   10                  15

<210> SEQ ID NO 29
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 29

Asp Leu Ser Leu Lys Glu Gly Ala Cys Asp Glu Leu Phe Ser Tyr
1               5                   10                  15

<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ala Cys Asp Glu Leu Phe Ser Tyr Leu Met Glu Lys Val Lys Arg
1               5                   10                  15

<210> SEQ ID NO 31
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Tyr Leu Met Glu Lys Val Lys Arg Gln Lys Asn Val Leu His Leu
1               5                   10                  15

<210> SEQ ID NO 32
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Arg Gln Lys Asn Val Leu His Leu Cys Cys Lys Lys Leu Lys Ile
1               5                   10                  15

<210> SEQ ID NO 33
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Leu Cys Cys Lys Lys Leu Lys Ile Phe Ala Met Pro Met Gln Asp
1               5                   10                  15

<210> SEQ ID NO 34
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ile Phe Ala Met Pro Met Gln Asp Ile Lys Met Ile Leu Lys Met
```

<210> SEQ ID NO 35
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 35

Asp Ile Lys Met Ile Leu Lys Met Val Gln Leu Asp Ser Ile Glu
1               5                   10                  15

<210> SEQ ID NO 36
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 36

Glu Asp Leu Glu Val Thr Cys Thr Trp Lys Leu Pro Thr Leu Ala
1               5                   10                  15

<210> SEQ ID NO 37
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 37

Thr Trp Lys Leu Pro Thr Leu Ala Lys Phe Ser Pro Tyr Leu Gly
1               5                   10                  15

<210> SEQ ID NO 38
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

Ala Ser Ala Thr Leu Gln Asp Leu Asp Phe Asp Glu Cys Gly Ile
1               5                   10                  15

<210> SEQ ID NO 39
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 39

Leu Asp Phe Asp Glu Cys Gly Ile Met Asp Asp Gln Leu Leu Val
1               5                   10                  15

<210> SEQ ID NO 40

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ile Met Asp Asp Gln Leu Leu Val Leu Leu Pro Ser Leu Ser His
1               5                   10                  15

<210> SEQ ID NO 41
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Val Leu Leu Pro Ser Leu Ser His Cys Ser Gln Leu Thr Thr Leu
1               5                   10                  15

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

His Cys Ser Gln Leu Thr Thr Leu Ser Phe Cys Gly Asn Pro Ile
1               5                   10                  15

<210> SEQ ID NO 43
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Leu Ser Phe Cys Gly Asn Pro Ile Ser Ile Ser Val Leu Gln Asn
1               5                   10                  15

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Asn Leu Leu His His Leu Ile Gly Leu Ser Asn Leu Thr His Val
1               5                   10                  15

<210> SEQ ID NO 45
<211> LENGTH: 15
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 45

Gly Leu Ser Asn Leu Thr His Val Leu Tyr Pro Val Pro Leu Glu
1               5                   10                  15

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Glu Ser Tyr Glu Asp Val His Gly Thr Leu His Leu Gly Arg Leu
1               5                   10                  15

<210> SEQ ID NO 47
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gly Thr Leu His Leu Gly Arg Leu Ala Tyr Leu His Ala Arg Leu
1               5                   10                  15

<210> SEQ ID NO 48
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Leu Ala Tyr Leu His Ala Arg Leu Arg Glu Leu Leu Cys Glu Leu
1               5                   10                  15

<210> SEQ ID NO 49
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Leu Arg Glu Leu Leu Cys Glu Leu Gly Arg Pro Ser Met Val Trp
1               5                   10                  15

<210> SEQ ID NO 50
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 50

Leu Gly Arg Pro Ser Met Val Trp Leu Ser Ala Asn Pro Cys Pro
1               5                   10                  15

<210> SEQ ID NO 51
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Pro His Cys Gly Asp Arg Thr Phe Tyr Asp Pro Glu Pro Ile Leu
1               5                   10                  15

<210> SEQ ID NO 52
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Phe Tyr Asp Pro Glu Pro Ile Leu Cys Pro Cys Phe Met Pro Asn
1               5                   10                  15

<210> SEQ ID NO 53
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ala Leu Tyr Val Asp Ser Leu Phe Phe Leu
1               5                   10

<210> SEQ ID NO 54
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Val Leu Asp Gly Leu Asp Val Leu Leu
1               5

<210> SEQ ID NO 55
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ser Leu Tyr Ser Phe Pro Glu Ala
1               5
```

```
<210> SEQ ID NO 56
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ser Leu Leu Gln His Ile Leu Gly Leu
1               5

<210> SEQ ID NO 57
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Asn Leu Thr His Val Leu Tyr Pro Val
1               5

<210> SEQ ID NO 58
<211> LENGTH: 5
<212> TYPE: PRT
<213> ORGANISM: Homo sapiens

<400> SEQUENCE: 58

Leu Asp Val Leu Leu
1               5

<210> SEQ ID NO 59
<211> LENGTH: 5
<212> TYPE: PRT
<213> ORGANISM: Homo sapiens

<400> SEQUENCE: 59

Leu Arg Arg Leu Leu
1               5

<210> SEQ ID NO 60
<211> LENGTH: 5
<212> TYPE: PRT
<213> ORGANISM: Homo sapiens

<400> SEQUENCE: 60

Leu Asp Gln Leu Leu
1               5

<210> SEQ ID NO 61
<211> LENGTH: 5
<212> TYPE: PRT
<213> ORGANISM: Homo sapiens

<400> SEQUENCE: 61

Leu Gln Ala Leu Leu
1               5

<210> SEQ ID NO 62
<211> LENGTH: 5
<212> TYPE: PRT
```

<213> ORGANISM: Homo sapiens

<400> SEQUENCE: 62

Leu Leu Ala Leu Leu
1               5

<210> SEQ ID NO 63
<211> LENGTH: 5
<212> TYPE: PRT
<213> ORGANISM: Homo sapiens

<400> SEQUENCE: 63

Leu Gln Ser Leu Leu
1               5

<210> SEQ ID NO 64
<211> LENGTH: 13
<212> TYPE: PRT
<213> ORGANISM: Homo sapiens

<400> SEQUENCE: 64

Val Leu Asp Gly Leu Asp Val Leu Leu Ala Gln Glu Val
1               5                   10

<210> SEQ ID NO 65
<211> LENGTH: 13
<212> TYPE: PRT
<213> ORGANISM: Homo sapiens

<400> SEQUENCE: 65

Gln Met Ile Asn Leu Arg Arg Leu Leu Leu Ser His Ile
1               5                   10

<210> SEQ ID NO 66
<211> LENGTH: 13
<212> TYPE: PRT
<213> ORGANISM: Homo sapiens

<400> SEQUENCE: 66

Leu Arg Gly Arg Leu Asp Gln Leu Leu Arg His Val Met
1               5                   10

<210> SEQ ID NO 67
<211> LENGTH: 13
<212> TYPE: PRT
<213> ORGANISM: Homo sapiens

<400> SEQUENCE: 67

Ser Pro Glu Pro Leu Gln Ala Leu Leu Glu Arg Ala Ser
1               5                   10

<210> SEQ ID NO 68
<211> LENGTH: 13
<212> TYPE: PRT
<213> ORGANISM: Homo sapiens

<400> SEQUENCE: 68

Thr Asp Asp Gln Leu Leu Ala Leu Leu Pro Ser Leu Ser
1               5                   10

<210> SEQ ID NO 69
<211> LENGTH: 13
<212> TYPE: PRT
<213> ORGANISM: Homo sapiens

<400> SEQUENCE: 69

Ser Ile Ser Ala Leu Gln Ser Leu Leu Gln His Leu Ile
1               5                   10

<210> SEQ ID NO 70
<211> LENGTH: 13
<212> TYPE: PRT
<213> ORGANISM: Homo sapiens

<400> SEQUENCE: 70

Leu His Ala Arg Leu Arg Glu Leu Leu Cys Glu Leu Gly
1               5                   10

<210> SEQ ID NO 71
<211> LENGTH: 508
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Glu Arg Arg Arg Leu Arg Gly Ser Ile Gln Ser Arg Tyr Ile Ser Met
1               5                   10                  15

Ser Val Trp Thr Ser Pro Arg Arg Leu Val Glu Leu Ala Gly Gln Ser
                20                  25                  30

Leu Leu Lys Asp Glu Ala Leu Ala Ile Ala Ala Leu Glu Leu Leu Pro
            35                  40                  45

Arg Glu Leu Phe Pro Pro Leu Phe Met Ala Ala Phe Asp Gly Arg His
    50                  55                  60

Ser Gln Thr Leu Lys Ala Met Val Gln Ala Trp Pro Phe Thr Cys Leu
65                  70                  75                  80

Pro Leu Gly Val Leu Met Lys Gly Gln Gln Leu His Leu Glu Thr Phe
                85                  90                  95

Lys Ala Val Leu Asp Gly Leu Asp Val Leu Leu Ala Gln Glu Val Arg
            100                 105                 110

Pro Arg Arg Trp Lys Leu Glu Val Leu Asp Leu Arg Lys Asn Ser His
    115                 120                 125

Gln Asp Phe Trp Thr Val Trp Ser Gly Asn Arg Ala Ser Leu Tyr Ser
130                 135                 140

Phe Pro Glu Pro Glu Ala Ala Gln Pro Met Arg Lys Arg Lys Val
145                 150                 155                 160

Asp Gly Leu Ser Thr Glu Ala Glu Gln Pro Phe Thr Pro Ile Glu Val
                165                 170                 175

Leu Val Asp Leu Ser Leu Lys Glu Gly Ala Cys Asp Glu Leu Phe Ser
            180                 185                 190

Tyr Leu Met Glu Lys Val Lys Arg Gln Lys Asn Val Leu His Leu Cys
    195                 200                 205

Cys Lys Lys Leu Lys Ile Phe Ala Met Pro Met Gln Asp Ile Lys Met
210                 215                 220

Ile Leu Lys Met Val Gln Leu Asp Ser Ile Glu Asp Leu Glu Val Thr
225                 230                 235                 240

Cys Thr Trp Lys Leu Pro Thr Leu Ala Lys Phe Ser Pro Tyr Leu Gly
                245                 250                 255

Gln Met Ile Asn Leu Arg Arg Leu Leu Leu Ser His Ile His Ala Ser
            260                 265                 270

-continued

Ser Ser Ile Ser Pro Glu Lys Glu Glu Tyr Ile Ala Gln Phe Thr
            275                 280                 285

Ser Gln Phe Leu Ser Leu Gln Cys Leu Gln Ala Leu Tyr Val Asp Ser
    290                 295                 300

Leu Phe Phe Leu Arg Gly Arg Leu Asp Gln Leu Leu Arg His Val Met
305                 310                 315                 320

Asn Pro Leu Glu Thr Leu Ser Val Thr Asn Cys Arg Leu Ser Glu Gly
                325                 330                 335

Asp Val Met His Leu Ser Gln Ser Pro Asn Val Ser Gln Leu Ser Val
                340                 345                 350

Leu Ser Leu Ser Gly Val Met Leu Thr Asp Val Ser Pro Glu Pro Leu
            355                 360                 365

Gln Ala Leu Leu Glu Arg Ala Ser Ala Thr Leu Gln Asp Leu Asp Phe
    370                 375                 380

Asp Glu Cys Gly Ile Met Asp Asp Gln Leu Leu Val Leu Leu Pro Ser
385                 390                 395                 400

Leu Ser His Cys Ser Gln Leu Thr Thr Leu Ser Phe Cys Gly Asn Pro
                405                 410                 415

Ile Ser Ile Ser Val Leu Gln Asn Leu Leu His His Leu Ile Gly Leu
                420                 425                 430

Ser Asn Leu Thr His Val Leu Tyr Pro Val Pro Leu Glu Ser Tyr Glu
            435                 440                 445

Asp Val His Gly Thr Leu His Leu Gly Arg Leu Ala Tyr Leu His Ala
    450                 455                 460

Arg Leu Arg Glu Val Val Cys Glu Leu Gly Arg Pro Ser Met Val Trp
465                 470                 475                 480

Leu Ser Ala Asn Pro Cys Pro His Cys Gly Asp Arg Thr Phe Tyr Asp
                485                 490                 495

Pro Glu Pro Ile Leu Cys Pro Cys Phe Met Pro Asn
                500                 505

<210> SEQ ID NO 72
<211> LENGTH: 509
<212> TYPE: PRT
<213> ORGANISM: Homo sapiens

<400> SEQUENCE: 72

Met Glu Arg Arg Arg Leu Arg Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

Ser Leu Leu Lys Asp Glu Ala Leu Ala Ile Ala Ala Leu Glu Leu Leu
        35                  40                  45

Pro Arg Glu Leu Phe Pro Pro Leu Phe Met Ala Ala Phe Asp Gly Arg
    50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
                100                 105                 110

Arg Pro Arg Arg Trp Lys Leu Gln Val Leu Asp Leu Arg Lys Asn Ser
            115                 120                 125

His Gln Asp Phe Trp Thr Val Trp Ser Gly Asn Arg Ala Ser Leu Tyr
    130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
            165                 170                 175

Val Leu Val Asp Leu Phe Leu Lys Glu Gly Ala Cys Asp Glu Leu Phe
        180                 185                 190

Ser Tyr Leu Ile Glu Lys Val Lys Arg Lys Asn Val Leu Arg Leu
    195                 200                 205

Cys Cys Lys Lys Leu Lys Ile Phe Ala Met Pro Met Gln Asp Ile Lys
210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
            260                 265                 270

Ser Ser Tyr Ile Ser Pro Glu Lys Glu Glu Gln Tyr Ile Ala Gln Phe
    275                 280                 285

Thr Ser Gln Phe Leu Ser Leu Gln Cys Leu Gln Ala Leu Tyr Val Asp
290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
355                 360                 365

Leu Gln Ala Leu Leu Glu Arg Ala Ser Ala Thr Leu Gln Asp Leu Val
    370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
    435                 440                 445

Glu Asp Ile His Gly Thr Leu His Leu Glu Arg Leu Ala Tyr Leu His
450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
            500                 505

<210> SEQ ID NO 73
<211> LENGTH: 509
<212> TYPE: PRT
<213> ORGANISM: Homo sapiens
<220> FEATURE:
<221> NAME/KEY: MOD_RES
<222> LOCATION: (47)..(47)
<223> OTHER INFORMATION: Any amino acid

<400> SEQUENCE: 73

```
Met Glu Arg Arg Arg Leu Trp Gly Ser Ile Gln Ser Arg Tyr Ile Ser
1               5                   10                  15
Met Ser Val Trp Thr Ser Pro Arg Arg Leu Val Glu Leu Ala Gly Gln
            20                  25                  30
Ser Leu Leu Lys Asp Glu Ala Leu Ala Ile Ala Ala Leu Glu Xaa Leu
        35                  40                  45
Pro Arg Glu Leu Phe Pro Pro Leu Phe Met Ala Ala Phe Asp Gly Arg
    50                  55                  60
His Ser Gln Thr Leu Lys Ala Met Val Gln Ala Trp Pro Phe Thr Cys
65                  70                  75                  80
Leu Pro Leu Gly Val Leu Met Lys Gly Gln His Leu His Leu Glu Thr
                85                  90                  95
Phe Lys Ala Val Leu Asp Gly Leu Asp Val Leu Leu Ala Gln Glu Val
            100                 105                 110
Arg Pro Arg Arg Trp Lys Leu Gln Val Leu Asp Leu Arg Lys Asn Ser
        115                 120                 125
His Gln Asp Phe Trp Thr Val Trp Ser Gly Asn Arg Ala Ser Leu Tyr
    130                 135                 140
Ser Phe Pro Glu Pro Glu Ala Ala Gln Pro Met Thr Lys Lys Arg Lys
145                 150                 155                 160
Val Asp Gly Leu Ser Thr Glu Ala Glu Gln Pro Phe Ile Pro Val Glu
                165                 170                 175
Val Leu Val Asp Leu Phe Leu Lys Glu Gly Ala Cys Asp Glu Leu Phe
            180                 185                 190
Ser Tyr Leu Ile Glu Lys Val Lys Arg Lys Asn Val Leu Arg Leu
        195                 200                 205
Cys Cys Lys Lys Leu Lys Ile Phe Ala Met Pro Met Gln Asp Ile Lys
210                 215                 220
Met Ile Leu Lys Met Val Gln Leu Asp Ser Ile Glu Asp Leu Glu Val
225                 230                 235                 240
Thr Cys Thr Trp Lys Leu Pro Thr Leu Ala Lys Phe Ser Pro Tyr Leu
                245                 250                 255
Gly Gln Met Ile Asn Leu Arg Arg Leu Leu Leu Ser His Ile His Ala
            260                 265                 270
Ser Ser Tyr Ile Ser Pro Glu Lys Glu Glu Gln Tyr Ile Ala Gln Phe
        275                 280                 285
Thr Ser Gln Phe Leu Ser Leu Gln Cys Leu Gln Ala Leu Tyr Val Asp
    290                 295                 300
Ser Leu Phe Phe Leu Arg Gly Arg Leu Asp Gln Leu Leu Arg His Val
305                 310                 315                 320
Met Asn Pro Leu Glu Thr Leu Ser Ile Thr Asn Cys Arg Leu Ser Glu
                325                 330                 335
Gly Asp Val Met His Leu Ser Gln Ser Pro Ser Val Ser Gln Leu Ser
            340                 345                 350
Val Leu Ser Leu Ser Gly Val Met Leu Thr Asp Val Ser Pro Glu Pro
        355                 360                 365
Leu Gln Ala Leu Leu Glu Arg Ala Ser Ala Thr Leu Gln Asp Leu Val
    370                 375                 380
Phe Asp Glu Cys Gly Ile Thr Asp Asp Gln Leu Leu Ala Leu Leu Pro
385                 390                 395                 400
Ser Leu Ser His Cys Ser Gln Leu Thr Thr Leu Ser Phe Tyr Gly Asn
```

Ser Ile Ser Ile Ser Ala Leu Gln Ser Leu Leu Gln His Leu Ile Gly
                420                 425                 430

Leu Ser Asn Leu Thr His Val Leu Tyr Pro Val Pro Leu Glu Ser Tyr
                435                 440                 445

Glu Asp Ile His Gly Thr Leu His Leu Glu Arg Leu Ala Tyr Leu His
                450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
                500                 505

<210> SEQ ID NO 74
<211> LENGTH: 509
<212> TYPE: PRT
<213> ORGANISM: Homo sapiens

<400> SEQUENCE: 74

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
                35                  40                  45

Pro Arg Glu Leu Phe Pro Pro Leu Phe Met Ala Ala Phe Asp Gly Arg
                50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
                100                 105                 110

Arg Pro Arg Arg Trp Lys Leu Gln Val Leu Asp Leu Arg Lys Asn Ser
                115                 120                 125

His Gln Asp Phe Trp Thr Val Trp Ser Gly Asn Arg Ala Ser Leu Tyr
                130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
                180                 185                 190

Ser Tyr Leu Ile Glu Lys Val Lys Arg Lys Lys Asn Val Leu Arg Leu
                195                 200                 205

Cys Cys Lys Lys Leu Lys Ile Phe Ala Met Pro Met Gln Asp Ile Lys
210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
                260                 265                 270

```
Ser Ser Tyr Ile Ser Pro Glu Lys Glu Glu Gln Tyr Ile Ala Gln Phe
            275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
                340                 345                 350

Val Leu Ser Leu Ser Gly Val Met Leu Thr Asp Val Ser Pro Glu Pro
            355                 360                 365

Leu Gln Ala Leu Leu Glu Arg Ala Ser Ala Thr Leu Gln Asp Leu Val
    370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
                420                 425                 430

Leu Ser Asn Leu Thr His Val Leu Tyr Pro Val Pro Leu Glu Ser Tyr
            435                 440                 445

Glu Asp Ile His Gly Thr Leu His Leu Glu Arg Leu Ala Tyr Leu His
            450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
                500                 505
```

CANCER VACCINES TARGETING PRAME AND USES THEREOF

CROSS-REFERENCE TO RELATED APPLICATIONS

This application claims priority to and the benefit of U.S. Provisional Patent Application No. 62/598,290, filed Dec. 13, 2017, the disclosure of which is incorporated herein by reference in its entirety.

SEQUENCE LISTING

This application contains a Sequence Listing which has been submitted electronically in ASCII format and is hereby incorporated by reference in its entirety. Said ASCII copy, created Dec. 8, 2020, is named 104409_000451_substitute_sequence_listing.txt and is 42,816 bytes in size.

TECHNICAL FIELD

The present invention relates to Preferentially Expressed Antigen in Melanoma (PRAME) antigens and nucleic acid molecules which encode the same. The present invention also relates to vaccines including such PRAME immunogens and/or nucleic acid molecules. The present invention further relates to methods of using the vaccines for inducing immune responses and preventing and/or treating subjects having cancer cells and tumors that express PRAME.

BACKGROUND

Cancer is among the leading causes of death worldwide and, in the United States, is the second most common cause of death, accounting for nearly one of every four deaths. The cancer vaccine market is growing rapidly. Effective tumor vaccines may be useful to prevent tumor growth and/or may be useful as being a more effective, less toxic alternative to standard treatments for patients with advanced cancers. An antigen associated with cancer and, therefore, a target for anti-tumor vaccines is PRAME.

PRAME, originally identified as a gene encoding a HLA-A24 restricted antigenic peptide in human melanoma, triggers autologous cytotoxic T cell-medicated immune responses. The human PRAME gene, located on chromosome 22 (HSA22), encodes a protein with seven leucine-rich (LXXLL (SEQ ID NO: 3)) motifs through which PRAME interferes with the retinoic acid receptor (RAR) pathway, and leads to the inhibition of RA-induced differentiation, growth arrest, and apoptosis (Epping, M. T. et al. The human tumor antigen PRAME is a dominant repressor of retinoic acid receptor signaling. Cell 122, 835-847, doi:10.1016/j.cell.2005.07.003 (2005)). In this way, PRAME functions as a transcriptional repressor of signaling pathways, and the over-expression of PRAME results in tumorigenesis.

Because its expression is low or absent in almost all normal adult tissues except for testis, PRAME is considered a cancer testis antigen (CTA). In addition to melanoma, PRAME is overexpressed in a variety of other human malignancies, including acute and chronic leukemia, multiple myeloma, medulloblastoma, sarcomas, head and neck cancer, breast cancer, non-small cell lung cancer, renal and ovarian cancer. In a study of ovarian carcinoma, PRAME expression was identified in 100% of surgical samples (n=27) (Brenne, K., Nymoen, D. A., Reich, R. & Davidson, B. PRAME (preferentially expressed antigen of melanoma) is a novel marker for differentiating serous carcinoma from malignant mesothelioma. American journal of clinical pathology 137, 240-247, doi:10.1309/AJCPGA95KVSAUDMF (2012)).

Prevention, diagnosis, and treatment of cancer may take many different forms. Prevention may include screening for pre-disposing factors (e.g., specific genetic variants), altering behavior (e.g., smoking, diet, and amount of physical activity), and vaccination against viruses (e.g., human papilloma virus hepatitis B virus). Treatment may include chemotherapy, radiation therapy, and surgical removal of a tumor or cancerous tissue. Despite the availability of numerous prevention and treatment methods, such methods often meet with limited success in effectively preventing and/or treating the cancer.

Vaccines for the treatment and prevention of cancer are of interest. However, existing vaccines targeting tumor cell antigens are limited by poor antigen expression in vivo. Accordingly, a need remains in the art for safe and effective vaccines and methods of their use for preventing and/or treating cancer and reducing mortality in subjects suffering from cancer.

SUMMARY OF THE INVENTION

The present disclosure is directed to nucleic acid molecules comprising SEQ ID NO:1 and nucleic acid molecules encoding the amino acid sequence set forth in SEQ ID NO:2. In some embodiments, the nucleic acid molecule comprises the nucleic acid sequence set forth in SEQ ID NO: 1. In further embodiments, the nucleic acid molecules comprise the nucleic acid sequence set forth in nucleotides 55 to 1584 of SEQ ID NO: 1. In still further embodiments, the nucleic acid molecule comprises a nucleic acid sequence that encodes the amino acid sequence set forth in SEQ ID NO: 2. In further embodiments, the nucleic acid molecule comprises a nucleic acid sequence that encodes the amino acid sequence as set forth in amino acid residues 19 to 526 of SEQ ID NO: 2. In still further embodiments, the vector comprises the nucleic acid molecule of claim 1.

In still further embodiments, the nucleic acid molecules encode a PRAME antigen. In some embodiments, the encoded PRAME antigen comprises the amino acid sequence set forth in amino acid residues 19 to 526 of SEQ ID NO: 2. In some embodiments, the encoded PRAME antigen comprises SEQ ID NO: 2.

The nucleic acid molecules described herein may be incorporated into a vector, such as a plasmid or viral vector. In some embodiments, the vector comprises the nucleic acid sequence set forth in SEQ ID NO: 1. In certain embodiments, the vector comprises the nucleic acid sequence set forth in nucleotides 55 to 1584 of SEQ ID NO: 1. In further embodiments, the vector comprises a nucleic acid sequence that encodes the amino acid sequence set forth in SEQ ID NO: 2. In still further embodiments, the vector comprises a nucleic acid sequence that encodes the amino acid sequence as set forth in amino acid residues 19 to 526 of SEQ ID NO: 2. In certain embodiments, the vector comprises the nucleic acid molecule of claim 1.

In some embodiments, the nucleic acids described herein are operably linked to a regulatory element. In some embodiments the regulatory element is a promoter and/or a poly-adenylation signal. In further embodiments, the promoter is a human cytomegalovirus immediate-early promoter (hCMV promoter). In still further embodiments, the poly-adenylation signal is a bovine growth hormone poly-adenylation signal (bGH polyA).

Further provided herein is a PRAME antigenic protein comprising the amino acid sequence set forth in amino acid residues 19 to 526 of SEQ ID NO: 2. In some embodiments, the PRAME antigen comprises SEQ ID NO: 2.

Vaccines comprising a PRAME antigen, wherein the antigen comprises the amino acid sequence set forth in amino acid residues 19 to 526 of SEQ ID NO: 2 are also provided. In some embodiments, the PRAME antigen comprises SEQ ID NO: 2. In some embodiments, the PRAME antigen is encoded by nucleotides 55 to 1584 of SEQ ID NO: 1. In some embodiments, the PRAME antigen is encoded by a nucleic acid molecule comprising SEQ ID NO: 1.

Also provided herein are vaccines comprising a nucleic acid molecule encoding a disclosed PRAME antigen. In some embodiments, the encoded PRAME antigen comprises the amino acid sequence set forth in amino acid residues 19 to 526 of SEQ ID NO: 2. In some embodiments, the encoded PRAME antigen comprises SEQ ID NO: 2. In some embodiments, the PRAME antigen is encoded by nucleotides 55 to 1584 of SEQ ID NO: 1. In some embodiments, the PRAME antigen is encoded by a nucleic acid molecule comprising SEQ ID NO: 1. In some embodiments, the nucleic acid molecule is incorporated into a vector, including but not limited to a plasmid or viral vector.

The disclosed vaccines may further comprise a pharmaceutically acceptable excipient. In some embodiments, the vaccines may further comprise an adjuvant. In certain embodiments, the adjuvant is IL-12, IL-15, IL-28, or RANTES.

Further provided herein are methods for treating a subject having a cell characterized by aberrant PRAME expression comprising administering a therapeutically effective amount of the vaccine. In some embodiments, the administration includes an electroporation step. In other embodiments, the administration occurs at one or more sites on the subject.

Also described herein are methods of treating cancer in a subject, the method comprising administering a therapeutically effective amount of a vaccine to the subject. Methods are also provided for vaccinating a subject against cells characterized by aberrant PRAME expression comprising administering a vaccine in an amount effective to elicit an immune response. The vaccine administered in the methods taught in this disclosure comprise a nucleic acid as described above. In some embodiments, the administration includes an electroporation step. In other embodiments, the administration occurs at one or more sites on the subject.

In some embodiments, the nucleic acid molecules described herein are for use as a medicament. In some embodiments, the nucleic acid molecules described herein are for use as a medicament in the treatment of cancer. In some embodiments, the nucleic acid molecules described herein are for use in the preparation of a medicament. In some embodiments, the nucleic acid molecules described herein are for use in the preparation of a medicament for the treatment of cancer.

BRIEF DESCRIPTION OF THE DRAWINGS

FIG. 1A provides a graphical representation of the location of amino acid residue numbers of the seven putative nuclear receptor (NR) boxes (LXXLL motifs (SEQ ID NO:3)) in PRAME protein. FIG. 1A discloses SEQ ID NOS 58-63, and 4, respectively, in order of appearance.

FIG. 1B provides the amino acid sequence data, including adjacent amino acid residues, for each NR box. FIG. 1B discloses SEQ ID NOS 3 and 64-70, respectively, in order of appearance.

FIG. 2 provides a sequence alignment of a modified synthetic consensus PRAME with human PRAME sequences. FIG. 2 discloses SEQ ID NOS 71-74, and 74, respectively, in order of appearance.

FIGS. 9A and 9B show the CD4+ and CD8+ response for producing IFNγ in mice receiving pGX1411 compared to untreated controls, respectively. FIGS. 9C and 9D show the CD4+ and CD8+ response for producing CD107a+ in mice receiving pGX1411 compared to untreated controls, respectively. FIGS. 9E and 9F show the CD4+ and CD8+ response for producing TNFα in mice receiving pGX1411 compared to untreated controls, respectively.

FIG. 14A illustrates the mean IFNγ response with the immunized group over time. FIG. 14B illustrates the IFNγ responses for individual NHPs. FIG. 14C illustrates the IFNγ responses in the groups along with variation within the group. Timing of administration of pGX1421 and pGX6006 is indicated by arrows 1-4.

FIG. 15A graphically displays CD4+ T-cell response. FIG. 15B graphically depicts CD8+ response. FIG. 15C graphically depicts CD8+GrB+ T-cell response. FIG. 15D illustrates the shift in CD8+ T-cell phenotype after immunization.

FIG. 16A depicts IFNγ response in individual NHPs administered pGX1421. FIG. 16B illustrates IFNγ response in individual NHPs administered both pGX1421 and pGX6006. FIG. 16C provides a comparison of the responses depicted in FIGS. 16A and 16B. Timing of administration of pGX1421 and pGX1421 in combination with pGX6006 is indicated by arrows 1-4.

FIGS. 17A-17F illustrate the cellular immune responses induced by pGX1421 and pGX1421 in combination with pGX6006 as characterized by flow cytometry. FIG. 17A depicts minimal CD4+ response in any individual recipient, and FIG. 17B illustrates the difference in INFγ and TNFα between the groups. FIG. 17C depicts a greater CD8+ T-cell response for pGX1421/pGX6006 administration rather than pGX1421 administration alone, and FIG. 17D illustrates the difference in INFγ and TNFα between the groups. FIG. 17E depicts the CD8+GrB+ T-cell response in NHPs administered pGX1421 alone or in combination with pGX6006, and FIG. 17F illustrates the difference in INFγ and TNFα between the groups.

FIG. 18C combines the data of FIGS. 18A and 18B for ease of comparison. Timing of administration of pGX1421 in combination with pGX6006 and pGX1411 in combination with pGX6006 is indicated by arrows 1-4.

FIGS. 19A-19F illustrate the cellular immune responses induced by administration of pGX1421 in combination with pGX6006 and those same responses induced by administration of pGX1411 in combination with pGX6006. Specifically, FIG. 19A illustrates the CD4+ T-cell responses induced by administration of pGX1421 in combination with pGX6006 and the CD4+ T-cell responses induced by administration of pGX1411 in combination with pGX6006, and FIG. 19D illustrates in INFγ and TNFα between these two groups. FIG. 19B illustrates the CD8+ T-cell responses induced by administration of pGX1421 in combination with pGX6006 and the CD8+ T-cell responses induced by administration of pGX1411 in combination with pGX6006, and FIG. 19E illustrates in INFγ and TNFα between these two groups. FIG. 19C illustrates the CD8+GrB+ T-cell responses induced by administration of pGX1421 in combination with pGX6006 and the CD8+GrB+ T-cell responses induced by administration of pGX1411 in combination with pGX6006, and FIG. 19F illustrates in INFγ and TNFα between the groups.

DETAILED DESCRIPTION OF THE INVENTION

Figures 1A, 1B:
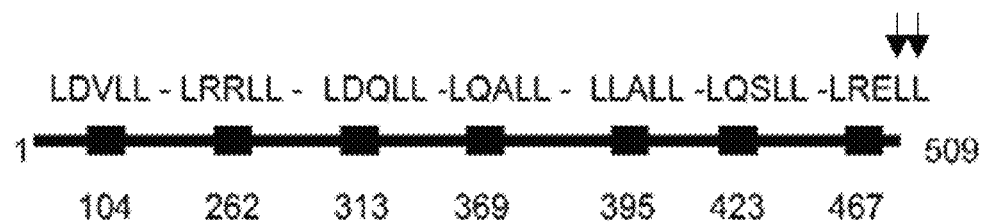
FIG. 1A and FIG. 1B depict schematic representation of PRAME.

The present invention relates to vaccines comprising a PRAME antigen. The vaccines provide treatment and/or prevention for a cancer expressing PRAME. The vaccine of the invention can provide any combination of particular cancer antigens for the particular prevention or treatment of the cancer of a subject that is in need of treatment.

One manner for designing the nucleic acid and its encoded amino acid sequence of the recombinant cancer antigen is by introducing mutations that change particular amino acids in the overall amino acid sequence of the native cancer antigen. The introduction of mutations does not alter the cancer antigen so much that it cannot be universally applied across a mammalian subject, and preferably a human or dog subject, but changes it enough that the resulting amino acid sequence breaks tolerance or is considered a foreign antigen in order to generate an immune response. Another manner may be creating a consensus recombinant cancer antigen that has at least 85% and up to 99% amino acid sequence identity to its corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its corresponding native cancer antigen. The native cancer antigen is the antigen normally associated with the particular cancer or cancer tumor. Depending upon the cancer antigen, the consensus sequence of the cancer antigen can be across mammalian species or within subtypes of a species or across viral strains or serotypes. Some cancer antigens do not vary greatly from the wild type amino acid sequence of the cancer antigen. Some cancer antigens have nucleic acid/amino acid sequences that are so divergent across species, that a consensus sequence cannot be generated. In these instances, a recombinant cancer antigen that will break tolerance and generate an immune response is generated that has at least 85% and up to 99% amino acid sequence identity to its corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its corresponding native cancer antigen. The aforementioned approaches can be combined so that the final recombinant cancer antigen has a percent similarity to native cancer antigen amino acid sequence as discussed above.

The PRAME antigen of the present disclosure can be a synthetic consensus PRAME antigen derived from the amino acid or nucleic acid sequences of PRAME from different species or from different isoforms within a species, and thus, the synthetic consensus PRAME antigen is non-native. The synthetic consensus PRAME antigen also comprises amino acid substitutions in the protein domain that interacts with or mediates interaction with retinoic acid receptor (RAR). Specifically, leucine amino acid residues at amino acid residues 487 and 488 may be substituted for by valine residues. Additionally, the PRAME antigen may comprise a Kozak regulatory sequence and/or an IgE leader sequence to enhance the expression and immunogenicity, respectively.

The recombinant PRAME can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

The vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses. Overall, by designing the cancer antigens to be recognized by the immune system helps to overcome other forms of immune suppression by tumor cells, and these vaccines can be used in combination with suppression or inhibition therapies (such as anti-PD-1 and anti-PDL-1 antibody therapies) to further increase T-cell and/or B-cell responses.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For recitation of numeric ranges herein, each intervening value having the same degree of precision as the recited range minimum and maximum is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the vaccines described herein to enhance the immunogenicity of the PRAME antigens antigens and/or the nucleic acid molecules encoding the antigens as described herein described herein.

"Antibody" as used herein means an antibody of classes IgG, IgM, IgA, IgD, or IgE, or fragments, or derivatives thereof, including Fab, F(ab')2, Fd, and single chain antibodies, diabodies, bispecific antibodies, bifunctional antibodies, and derivatives thereof. The antibody can be an antibody isolated from the serum sample of a mammal, a polyclonal antibody, an affinity purified antibody, or any mixture thereof which exhibits sufficient binding specificity to a desired epitope or a sequence derived therefrom.

"PRAME Antigen" refers to: proteins having mutated PRAME amino acid sequences including amino acid residues 19 to 526 of SEQ ID NO:2. PRAME antigens may optionally include signal peptides such as those from other proteins. For example, a PRAME antigen comprising a signal peptide may include the amino acid sequence set forth in SEQ ID NO: 2.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of a subject or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple sequences for the same gene from different organisms. Nucleic acid sequences that encode a consensus polypeptide sequence can be prepared. Vaccines comprising proteins that comprise consensus sequences and/or nucleic acid molecules that encode such proteins can be used to induce broad immunity against an antigen.

"Constant current" as used herein describes a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below, excluding an heterologous signal peptide added. The fragment may comprise at least 95%, at least 96%, at least 97%, at least 98%, or at least 99% of one or more of the nucleic acid sequences set forth below and additionally optionally comprise sequence encoding a heterologous signal peptide which is not included when calculating percent identity. Fragments may further comprise coding sequences for a signal peptide such as an immunoglobulin signal peptide, for example an IgE or IgG signal peptide. The coding sequence encoding an N terminal methionine and/or signal peptide may be linked to a fragment of coding sequence.

In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

"Fragment" or "immunogenic fragment" with respect to polypeptide sequences means a polypeptide capable of eliciting an immune response in a mammal that cross reacts with an antigen disclosed herein. The fragments can be polypeptide fragments selected from at least one of the various amino acids sequences below. Fragments of consensus proteins can comprise at least 10%, at least 20%, at least 30%, at least 40%, at least 50%, at least 60%, at least 70%, at least 80%, at least 90% or at least 95% of a consensus protein, excluding any heterologous signal peptide added. The fragment may comprise at least 95%, at least 96%, at least 97%, at least 98%, or at least 99% of one or more of the amino sequences set forth below and additionally optionally comprise a heterologous signal peptide which is not included when calculating percent identity. Fragments may further comprise a signal peptide such as an immunoglobulin signal peptide, for example an IgE or IgG signal peptide.

In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a protein sequence disclosed herein.

As used herein, the term "genetic construct" refers to the DNA or RNA molecules that comprise a nucleotide sequence that encodes a protein. The coding sequence includes initiation and termination signals operably linked to regulatory elements including a promoter and polyadenylation signal capable of directing expression in the cells of the subject to whom the nucleic acid molecule is administered. As used herein, the term "expressible form" refers to a gene construct that contain the necessary regulatory elements operably linked to a coding sequence that encodes a protein such that, when present in cell of a subject, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally derived molecule which is capable of conferring, activating, or enhancing expression of a nucleic acid in a cell. A promoter can comprise one or more specific transcriptional regulatory sequences to further enhance expression and/or to alter the spatial expression and/or temporal expression of a nucleic acid in a cell. A promoter can also comprise distal enhancer or repressor elements, which can be located as much as several thousand base pairs from the start site of transcription. A promoter can be derived from sources including viral, bacterial, fungal, plant, insect, and animal. A promoter can regulate the expression of a gene component constitutively or differentially with respect to cell, tissue, or organ in which expression occurs, or with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described vaccines. The mammal can be a human, chimpanzee, dog, cat, horse, cow, mouse, or rat.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treat," "treatment," or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

"Variant" as used herein with respect to a peptide or polypeptide means a peptide or polypeptide that differs in amino acid sequence by the insertion, deletion, or conservative substitution of amino acids, but retains at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome, or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

Vaccine

Provided herein are vaccines comprising a herein-described PRAME antigen or a nucleic acid molecule encoding such an antigen. In some embodiments, the PRAME antigen comprises the amino acid sequence set forth in amino acid residues 19 to 526 of SEQ ID NO: 2. In some embodiments, the nucleic acid molecule encodes a PRAME antigen having the amino acid sequence set forth in amino acid residues 19 to 526 SEQ ID NO:2. In some embodiments, the PRAME antigen comprises the amino acid sequence set forth in SEQ ID NO: 2. In some embodiments, the nucleic acid molecule encodes a PRAME antigen having the amino acid sequence set forth SEQ ID NO:2. In some embodiments, the nucleic acid molecule encoding the PRAME antigen comprises the nucleic acid sequence set forth in nucleotides 55 to 1584 of SEQ ID NO: 1. In some embodiments, the nucleic acid molecule encoding the PRAME antigen comprises the nucleic acid sequence set forth in SEQ ID NO: 1. The vaccines can be capable of generating in a subject an immune response against the antigen. The immune response can be a therapeutic or prophylactic immune response. The vaccines may comprise a vector or a plurality of vectors as described in more detail below.

The vaccines can be used to protect against cancer, for example, a cancer or tumor expressing PRAME. The vaccines can be used to prevent and/or treat an ovarian cancer expressing PRAME in a subject in need thereof. The vaccines can induce cellular and/or antibody responses against PRAME and against cancers expressing PRAME in a subject in need thereof. In some embodiments of the present disclosure, the vaccine can be used to protect against, prevent, treat, and/or induce cellular and/or antibody responses against cells characterized by aberrant expression of PRAME. In some embodiments of the present disclosure, the vaccine can be used to protect against, prevent, treat, and/or induce cellular and/or antibody responses against ovarian cancer cells characterized by aberrant expression of PRAME, specifically epithelial ovarian cancer cells, and more specifically, serous ovarian cancer cells.

The development of a cancer vaccine as described herein comprises identifying a cancer antigen, e.g., PRAME, that is not recognized by the immune system and is a self-antigen. The cancer antigen identified is changed from a self-antigen to a foreign antigen in order to be recognized by the immune system. The redesign of the nucleic acid and amino acid sequence of the recombinant cancer antigen from a self to a foreign antigen breaks tolerance of the antigen by the immune system. In order to break tolerance, several redesign measures can be employed to produce the cancer antigen as described below.

The breaking of tolerance can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that downregulate MHC presentation, factors that upregulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

In a particular embodiment, the vaccine can mediate clearance or prevent growth of tumor cells by (1) increasing cytotoxic T lymphocyte such as CD8$^+$ (CTL) to attack and kill tumor cells; (2) increasing T helper cell responses; and/or (3) increasing inflammatory responses via IFN-γ and TFN-α, or preferably all of the aforementioned. The vaccine can increase tumor-free survival by 30%, 31%, 32%, 33%, 34%, 35%, 36%, 37%, 38%, 39%, 40%, 41%, 42%, 43%, 44%, and 45%. The vaccine can reduce tumor mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% after immunization. The vaccine can prevent and block increases in monocyte chemoattractant protein 1 (MCP-1), a cytokine secreted by myeloid derived suppressor cells. The vaccine can increase tumor survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60%.

The vaccine can increase a cellular immune response in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine. In some embodiments the vaccine can increase the cellular immune response in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the vaccine.

The vaccine can increase interferon gamma (IFN-γ) levels in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the vaccine. In some embodiments the vaccine can increase IFN-γ levels in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the vaccine.

The vaccine can be a DNA vaccine. DNA vaccines are disclosed in U.S. Pat. Nos. 5,593,972; 5,739,118; 5,817,637; 5,830,876; 5,962,428; 5,981,505; 5,580,859; 5,703,055; and 5,676,594, which are incorporated herein fully by reference. The DNA vaccine can further comprise elements or reagents that inhibit it from integrating into the chromosome.

The vaccine can include an RNA encoding the cancer antigen. The RNA vaccine can be introduced into the cell.

The vaccine can be an attenuated live vaccine, a vaccine using recombinant vectors to deliver antigen, subunit vaccines, and glycoprotein vaccines, for example, but not limited to, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

In some embodiments, the nucleic acid vaccine may further comprise coding sequence for a molecular adjuvant, in some cases the molecular adjuvant can be IL-12, IL-15, IL-28, IL-31, IL-33, and/or RANTES, and in some cases the molecular adjuvant is a checkpoint inhibitor, including anti-cytotoxic T-lymphocyte antigen 4 (CTLA-4), anti-programmed death receptor-1 (PD-1) and anti-lymphocyte-activation gene (LAG-3). Coding sequence for IL-12, IL-15, IL-28, IL-31, IL-33 and/or RANTES may be included on one or more nucleic acid molecules that comprise coding sequence for one or more antigens. Coding sequence for IL-12, IL-15, IL-28, IL-31, IL-33, and/or RANTES may be included on a separate nucleic acid molecules such as a separate plasmid.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose. The vaccine can accomplish some or all of these features by containing the cancer antigen as discussed below.

The vaccine can further comprise one or more inhibitors of one or more immune checkpoint molecules (i.e., an immune checkpoint inhibitor). Immune checkpoint molecules are described below in more detail. The immune checkpoint inhibitor is any nucleic acid or protein that prevents the suppression of any component in the immune system such as MHC class presentation, T cell presentation and/or differentiation, B cell presentation and/or differentiation, any cytokine, chemokine or signaling for immune cell proliferation and/or differentiation. As also described below in more detail, the vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses.

Antigen

As described above, the vaccine can comprise an antigen or a nucleic acid molecule encoding an antigen. The antigen can be PRAME, a fragment thereof, a variant thereof, or a combination thereof. PRAME is expressed in testis but not typically, or in relatively small amounts, in normal, noncancerous tissues. The PRAME protein is a repressor of retinoic acid receptor, and without being bound to theory, this repression is thought to confer a growth advantage to cancer cells by repressing retinoic acid induced arrest of cell proliferation and apoptosis. For example, PRAME has been associated with several forms of cancer and is a known cancer antigen. PRAME expression is increased in endometrial cancer, testis cancer, melanoma, and ovarian cancer.

Accordingly, the vaccine can be used for treating subjects suffering from PRAME-expressing cancer. The vaccine can also be used for treating subjects with cancers or tumors that express PRAME or preventing development of such tumors in subjects. The PRAME antigen of the present disclosure differs from the native, "normal" PRAME antigen, and thus provides therapy or prophylaxis against a PRAME antigen-expressing tumor. Accordingly, PRAME antigen sequences that differ from the native PRAME gene (i.e., variant PRAME genes or sequences) are provided herein. Some aspects of the present invention provide for vaccine comprising a nucleic acid molecule comprising the nucleic acid sequence set forth in SEQ ID NO: 1, and some aspects provide for a vaccine comprising a nucleic acid molecule comprising a nucleic acid sequence that encodes the amino acid sequence set forth in SEQ ID NO: 2.

Isolated nucleic acid molecules comprising the above-described heterologous sequences are provided. Isolated nucleic acid molecules consisting of the above-described heterologous sequences are provided. Isolated nucleic acid molecules comprising the above-described heterologous sequences may be incorporated into vectors such as plasmids, viral vectors and other forms of nucleic acid molecules as described below. Thus, in some embodiments of the present disclosure, nucleic acid molecule is incorporated into a plasmid. In other embodiments the nucleic acid molecule is incorporated into a vector. Some aspects of the present disclosure provide compositions comprising the nucleic acid having the nucleotide acid sequence SEQ ID NO:1 or having a nucleotide sequence encoding the amino acid sequence of SEQ ID NO:2.

Provided herein are nucleic acid molecules having sequences that encode PRAME antigens. In some embodiments, the nucleic acid molecule is incorporated into a vector, including but not limited to a plasmid or a viral vector. Coding sequences encoding PRAME antigens have the sequences as described above.

Protein molecules comprising the above described heterologous amino acid sequences are provided. Protein molecules consisting of the above described heterologous amino acid sequences are provided. Provided herein are proteins and polypeptides having the above-described sequences. The proteins and polypeptide of the present disclosure may be referred to as PRAME antigens and PRAME immunogens. PRAME antigens are capable of eliciting an immune response against cancers and/or tumors expressing a PRAME antigen.

In one aspect, it is desired that the consensus antigen provides for improved transcription and translation, including having one or more of the following: low GC content leader sequence to increase transcription; mRNA stability and codon optimization; and, to the extent possible, elimination of cis-acting sequence motifs (i.e., internal TATA-boxes).

In some aspects, it is desired to generate a consensus antigen that generates a broad immune response across multiple strains, the consensus antigen having one or more of the following: incorporate all available full-length sequences; computer generated sequences that utilize the most commonly occurring amino acid at each position; and increase cross-reactivity between strains.

The PRAME antigen can be a consensus antigen (or immunogen) sequence derived from two or more species. The PRAME antigen can comprise a consensus sequence and/or modification(s) for improved expression. Modification can include codon optimization, RNA optimization, addition of a Kozak sequence (e.g., GCC ACC) for increased translation initiation and/or the addition of an immunoglobulin leader sequence to increase the immunogenicity of the PRAME antigen. The PRAME antigen can comprise a signal peptide such as an immunoglobulin signal peptide, for example, but not limited to, an immunoglobulin E (IgE) or immunoglobulin G (IgG) signal peptide. In some embodiments, the PRAME consensus antigen can comprise a hemagglutinin (HA) tag. The PRAME consensus antigen can be designed to elicit stronger and broader cellular and/or humoral immune responses than a corresponding codon optimized PRAME antigen.

The PRAME consensus antigen can comprise one or more variants in one or more functional domains of the protein, thereby eliciting stronger and broader cellular and/or humoral immune responses than a corresponding codon optimized PRAME antigen. The one or more mutations can be a substitution of one or more of the amino acids in a domain of the PRAME protein that mediates interaction with RAR.

Vaccine in Combination with Immune Checkpoint Inhibitor

The vaccine can further comprise one or more inhibitors of one or more immune checkpoint molecules (i.e., an immune checkpoint inhibitor). Immune check point molecules are described below in more detail. The immune checkpoint inhibitor is any nucleic acid or protein that prevents the suppression of any component in the immune system such as MHC class presentation, T cell presentation and/or differentiation, B cell presentation and/or differentiation, any cytokine, chemokine or signaling for immune cell proliferation and/or differentiation.

Such an inhibitor can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

In some embodiments, the immune checkpoint inhibitor can be one or more nucleic acid sequences encoding an antibody, a variant thereof, a fragment thereof, or a combination thereof. In other embodiments, the immune check point inhibitor can be an antibody, a variant thereof, a fragment thereof, or a combination thereof 1. Immune Checkpoint Molecule The immune check point molecule can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

a. PD-1 and PD-L1

The immune checkpoint molecule may programmed cell death protein 1 (PD-1), programmed cell death ligand 1 (PD-L1), a fragment thereof, a variant thereof, or a combination thereof. PD-1 is a cell surface protein encoded by the PDCD1 gene. PD-1 is a member of the immunoglobulin superfamily and is expressed on T cells and pro-B cells, and thus, contributes to the fate and/or differentiation of these cells. In particular, PD-1 is a type 1 membrane protein of the CD28/CTLA-4 family of T cell regulators and negatively regulates T cell receptor (TCR) signals, thereby negatively regulating immune responses. PD-1 can negatively regulated CD8+ T cell responses, and thus inhibit CD8-mediated cytotoxicity and enhance tumor growth.

PD-1 has two ligands, PD-L1 and PD-L2, which are members of the B7 family. PD-L1 is unregulated on macrophages and dendritic cells (DCs) in response to LPS and GM-CSF treatment and on T cells and B cells upon TCR and B cell receptor signaling. PD-L1 is expressed by many tumor cell lines, including myelomas, mastocytomas, and melanomas.

2. Anti-Immune Checkpoint Molecule Antibody

As described above, the immune checkpoint inhibitor can be an antibody. The antibody can bind or react with an antigen (i.e., the immune checkpoint molecule described above.) Accordingly, the antibody may be considered an anti-immune checkpoint molecule antibody or an immune checkpoint molecule antibody. The antibody can be encoded by a nucleic acid sequence contained in The antibody can include a heavy chain polypeptide and a light chain polypeptide. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

The light chain polypeptide can include a variable light chain (VL) region and/or a constant light chain (CL) region. The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

Additionally, the proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

a. PD-1 Antibody

The anti-immune checkpoint molecule antibody can be an anti-PD-1 antibody (also referred to herein as "PD-1 antibody"), a variant thereof, a fragment thereof, or a combination thereof. The PD-1 antibody can be Nivolumab. The anti-PD-1 antibody can inhibit PD-1 activity, thereby inducing, eliciting, or increasing an immune response against a tumor or cancer and decreasing tumor growth.

b. PD-L1 Antibody

The anti-immune checkpoint molecule antibody can be an anti-PD-L1 antibody (also referred to herein as "PD-L1 antibody"), a variant thereof, a fragment thereof, or a combination thereof. The anti-PD-L1 antibody can inhibit PD-L1 activity, thereby inducing, eliciting, or increasing an immune response against a tumor or cancer and decreasing tumor growth.

Vector

The vaccine can comprise one or more vectors that include a heterologous nucleic acid encoding the PRAME antigen. The one or more vectors can be capable of expressing the antigen in a quantity effective to ealicit an immune response in the mammal. The vector may comprise heterologous nucleic acid encoding the antigen. The vector can have a nucleic acid sequence containing an origin of replication. The vector can be a plasmid, bacteriophage, bacterial artificial chromosome, or yeast artificial chromosome. The vector can be either a self-replication extra chromosomal vector or a vector that integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery. The plasmid is frequently engineered to contain regulatory sequences that act as enhancer and promoter regions and lead to efficient transcription of the gene carried on the expression vector. The vectors of the present invention express large amounts of stable messenger RNA and, therefore, proteins.

The vectors may have expression enhancers such as a strong promoter, a strong termination codon, adjustment of the distance between the promoter and the cloned gene, and the insertion of a transcription termination sequence and a PTIS (portable translation initiation sequence).

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence. The vector may comprise sequences that are required for, or enhance the efficiency of, cloning desired fragments including, but not limited to, PRAME antigen or other coding sequences, regulatory sequences, and selection and/or screening marker coding sequences, into the vector. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

The vector can be a plasmid. The plasmid may be useful for transfecting cells with nucleic acid encoding the PRAME antigen, and the transformed host cells are cultured and maintained under conditions wherein expression of the antigen takes place.

The plasmid may comprise a nucleic acid sequence that encodes one or more of the PRAME antigens disclosed herein including coding sequences that encode synthetic, consensus antigen capable of eliciting an immune response against an antigen, fragments of such proteins, variants of such proteins, fragments of variants or fusion proteins which are made up of combinations of consensus proteins and/or fragments of consensus protein and/or variants of consensus protein and/or fragments of variants consensus proteins.

A single plasmid may contain coding sequence for a single antigen, coding sequence for two antigens, coding sequence for three antigens, or coding sequence for four antigens.

In some embodiments, a plasmid may further comprise coding sequence that encodes CCR20 alone or as part of one these plasmids. Similarly, plasmids may further comprise coding sequences for IL-12, IL-15, and/or IL-28.

The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence. The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in U.S. Publication No. 2004/0175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human (3-globin polyadenylation signal. The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhancers are described in U.S. Pat. Nos. 5,593,972; 5,962,428; and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAXI, pCEP4 or pREP4 (Invitrogen, San Diego, Calif.). The plasmid may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may also comprise a regulatory sequence, which may be well suited for gene expression in a cell harboring the plasmid. The coding sequence may comprise a codon that may allow more efficient transcription of the coding sequence in the host cell.

The coding sequence may also comprise an immunoglobulin (Ig) leader sequence. The leader sequence may be 5' of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which may be used for protein production in mammalian cells such as Chinese hamster ovary (CHO) cells.

The vector may be circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be perM2. The LEC can be perNP. perNP and perMR can be derived from pNP (Puerto Rico/34) and pM2 (New Caledonia/99), respectively.

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

Methods of Preparing the Vector

Provided herein are methods for preparing the vector that comprises the nucleic acid molecules encoding a PRAME antigen discussed herein. The vector, after the final subcloning step into the mammalian expression plasmid, can be used to inoculate a cell culture in a large scale fermentation tank, using known methods in the art.

The vector for use with the EP devices, which are described below in more detail, can be formulated or manufactured using a combination of known devices and techniques, but preferably they are manufactured using an optimized plasmid manufacturing technique that is described in a licensed, co-pending U.S. application Ser. No. 12/126,611, filed on May 23, 2008. In some examples, the PRAME antigen-encoding nucleic acid molecules used in these studies can be formulated at concentrations greater than or equal to 10 mg/mL. The manufacturing techniques also include or incorporate various devices and protocols that are commonly known to those of ordinary skill in the art, in addition to those described in U.S. Application No. 60/939,792, including those described in a licensed patent, U.S. Pat. No. 7,238,522, issued on Jul. 3, 2007. The above-referenced application and patent, U.S. Application No. 60/939,792 and U.S. Pat. No. 7,238,522, respectively, are hereby incorporated in their entirety.

Excipients and Other Components of the Vaccine

The vaccine may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be one or more adjuvants. The adjuvant can be other genes that are expressed in an alternative plasmid or are delivered as proteins in combination with the plasmid above in the vaccine. The one or more adjuvants may be selected from the group consisting of: CCL20, α-interferon(IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), MHC, CD80, CD86, IL-1, IL-2, IL-4, IL-5, IL-6, IL-10, IL-12, IL-15, IL-18, IL-28, IL-33, MCP-1, MIP-1a, MIP-1-, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DRS, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, TAP2, IL-15 having the signal sequence or coding sequence that encodes the signal sequence deleted and optionally including a different signal peptide such as that from IgE or coding sequence that encodes a different signal peptide such as that from IgE, and functional fragments thereof, or a combination thereof. The adjuvant can be IL-12, IL-15, IL-28, IL-33, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

In some embodiments adjuvant may be one or more proteins and/or nucleic acid molecules that encode proteins selected from the group consisting of: CCL-20, IL-12, IL-15, IL-28, IL-33, CTACK, TECK, MEC or RANTES. Examples of IL-12 constructs and sequences are disclosed in PCT Application No. PCT/US1997/019502 and corresponding U.S. application Ser. No. 08/956,865, and PCT Application No. PCT/US2012/069017, filed Dec. 11, 2012, and corresponding U.S. application Ser. No. 14/365,086, filed Jun. 12, 2014, filed Dec. 12, 2011, and Ser. No. 15/055,002, filed Feb. 26, 2016, which are each incorporated herein by reference. Examples of IL-15 constructs and sequences are disclosed in PCT Application No. PCT/US04/18962 and corresponding U.S. application Ser. No. 10/560,650, and in PCT Application No. PCT/US07/00886 and corresponding U.S. application Ser. No. 12/160,766, and in PCT Application No. PCT/US10/048827, which are each incorporated herein by reference. Examples of IL-28 constructs and sequences are disclosed in PCT Application No. PCT/US09/039648 and corresponding U.S. application Ser. No. 12/936,192, which are each incorporated herein by reference. Examples of RANTES and other constructs and sequences are disclosed in PCT Application No. PCT/US1999/004332 and corresponding U.S. application Ser. No. 09/622,452, which are each incorporated herein by reference. Other examples of RANTES constructs and sequences are disclosed in PCT Application No. PCT/US11/024098, which is incorporated herein by reference. Examples of RANTES and other constructs and sequences are disclosed in PCT Application No. PCT/US1999/004332 and corresponding U.S. application Ser. No. 09/622,452, which are each incorporated herein by reference. Other examples of RANTES constructs and sequences are disclosed in PCT Application No. PCT/US11/024098, which is incorporated herein by reference. Examples of chemokines CTACK, TECK and MEC constructs and sequences are disclosed in PCT Application No. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

Other genes that can be useful as adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DRS, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof The vaccine may further comprise a genetic vaccine facilitator agent as described in U.S. Application No. 021,579, filed Apr. 1, 1994, which is fully incorporated by reference.

The vaccine may comprise the antigen and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, vaccine according to the present invention comprise about 5 nanogram to about 1000 micrograms of a nucleic acid molecule. In some preferred embodiments, vaccine can contain about 10 nanograms to about 800 micrograms of a nucleic acid molecule. In some preferred embodiments, the vaccine can contain about 0.1 to about 500 micrograms of a nucleic acid molecule. In some preferred embodiments, the vaccine can contain about 1 to about 350 micrograms of a nucleic acid molecule. In some preferred embodiments, the vaccine can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the antigen or plasmid thereof.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

Pharmaceutical Compositions of the Vaccine

The vaccine can be in the form of a pharmaceutical composition. The pharmaceutical composition can comprise the vaccine. The pharmaceutical compositions can comprise about 5 nanograms (ng) to about 10 milligrams (mg) of the nucleic acid molecule of the vaccine. In some embodiments, pharmaceutical compositions according to the present invention comprise about 25 ng to about 5 mg of the nucleic acid molecule of the vaccine. In some embodiments, the pharmaceutical compositions contain about 50 ng to about 1 mg of the nucleic acid molecule of the vaccine. In some embodiments, the pharmaceutical compositions contain about 0.1 to about 500 micrograms of the nucleic acid molecule of the vaccine. In some embodiments, the pharmaceutical compositions contain about 1 to about 350 micrograms of the nucleic acid molecule of the vaccine. In some embodiments, the pharmaceutical compositions contain about 5 to about 250 micrograms of the nucleic acid molecule of the vaccine. In some embodiments, the pharmaceutical compositions contain about 10 to about 200 micrograms of the nucleic acid molecule of the vaccine. In some embodiments, the pharmaceutical compositions contain about 15 to about 150 micrograms of the nucleic acid molecule of the vaccine. In some embodiments, the pharmaceutical compositions contain about 20 to about 100 micrograms of the nucleic acid molecule of the vaccine. In some embodiments, the pharmaceutical compositions contain about 25 to about 75 micrograms of the nucleic acid molecule of the vaccine. In some embodiments, the pharmaceutical compositions contain about 30 to about 50 micrograms of the nucleic acid molecule of the vaccine. In some embodiments, the pharmaceutical compositions contain about 35 to about 40 micrograms of the nucleic acid molecule of the vaccine. In some embodiments, the pharmaceutical compositions contain about 100 to about 200 micrograms of the nucleic acid molecule of the vaccine. In some embodiments, the pharmaceutical compositions comprise about 10 micrograms to about 100 micrograms of the nucleic acid molecule of the vaccine. In some embodiments, the pharmaceutical compositions comprise about 20 micrograms to about 80 micrograms of the nucleic acid molecule of the vaccine. In some embodiments, the pharmaceutical compositions comprise about 25 micrograms to about 60 micrograms of the nucleic acid molecule of the vaccine. In some embodiments, the pharmaceutical compositions comprise about 30 ng to about 50 micrograms of the nucleic acid molecule of the vaccine. In some embodiments, the pharmaceutical compositions comprise about 35 ng to about 45 micrograms of the nucleic acid molecule of the vaccine. In some preferred embodiments, the pharmaceutical compositions contain about 0.1 to about 500 micrograms of the nucleic acid molecule of the vaccine. In some preferred embodiments, the pharmaceutical compositions contain about 1 to about 350 micrograms of the nucleic acid molecule of the vaccine. In some preferred embodiments, the pharmaceutical compositions contain about 25 to about 250 micrograms of the nucleic acid molecule of the vaccine. In some preferred embodiments, the pharmaceutical compositions contain about 100 to about 200 micrograms of the nucleic acid molecule of the vaccine.

In some embodiments, pharmaceutical compositions according to the present invention comprise at least 10, 15, 20, 25, 30, 35, 40, 45, 50, 55, 60, 65, 70, 75, 80, 85, 90, 95 or 100 ng of the nucleic acid molecule of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95,100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms of DNA of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of the nucleic acid molecule of the vaccine.

In other embodiments, the pharmaceutical composition can comprise up to and including 15, 20, 25, 30, 35, 40, 45, 50, 55, 60, 65, 70, 75, 80, 85, 90, 95 or 100 ng of the nucleic acid molecule of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95,100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 micrograms of the nucleic acid molecule of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of the nucleic acid molecule of the vaccine.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The vaccine can further comprise a pharmaceutically acceptable excipient. The pharmaceutically acceptable excipient can be functional molecules such as vehicles, adjuvants, carriers, or diluents. The pharmaceutically acceptable excipient can be a transfection facilitating agent.

In some embodiments, the transfection facilitating agent is a polyanion, polycation, including poly-L-glutamate (LGS), or lipid. In one embodiment, the transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the transfection facilitating agent can comprise lipids, liposomes, including lecithin liposomes or other liposomes known in the art, as a DNA-liposome mixture (see for example WO/9324640), calcium ions, viral proteins, polyanions, polycations, or nanoparticles, or other known transfection facilitating agents. Concentration of the transfection agent in the vaccine can be less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

Methods of Vaccination

Provided herein are methods for treating and/or preventing PRAME-expressing cancer using the pharmaceutical formulations described above. Also described herein are methods of using the pharmaceutical formulations described above in the treatment and/or prevention of PRAME-expressing cancer in a subject. Also described herein are methods of vaccinating a subject. Also described herein are methods of administering the pharmaceutical formulations described herein to a subject in need thereof. The methods described herein collectively referred to as methods of treatment using the pharmaceutical formulations described herein can comprise administering one or more vaccine as described herein to a subject in need thereof to induce a therapeutic and/or prophylactic immune response. The vaccine can be administered to a subject to modulate the activity of the subject's immune system and enhance the immune response. The administration of the vaccine can be the transfection of the cancer antigens as disclosed herein as a nucleic acid molecule that is expressed in the transfected cell and delivered to the surface of the cell, whereupon the immune system recognizes the antigen and induces a cellular, humoral, or cellular and humoral response. The administration of the vaccine can be used to induce or elicit an immune response in subjects against one or more of the cancer antigens as disclosed herein by administering to the subject the vaccine as discussed herein.

The vaccine can be administered to a subject to modulate the activity of the subject's immune system, thereby enhancing the immune response. In some embodiments, the subject is a mammal. Upon administration of the vaccine to the mammal, and thereby introducing the vector into the cells of the mammal, the transfected cells will express and secrete one or more of the cancer antigens as disclosed herein. These secreted proteins, or synthetic antigens, will be recognized as foreign by the immune system, which will mount an immune response that can include: antibodies made against the one or more cancer antigens, and T-cell response specifically against the one or more cancer antigens. In some examples, a mammal vaccinated with the vaccines discussed herein will have a primed immune system and when challenged with the one or more cancer antigens as disclosed herein, the primed immune system will allow for rapid clearing of subsequent cancer antigens as disclosed herein, whether through the humoral, cellular, or both cellular and humoral immune responses.

Methods of administering the nucleic acid molecule of a vaccine are described in U.S. Pat. Nos. 4,945,050 and 5,036,006, both of which are incorporated herein in their entirety by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, and preferably human, cow, or pig. The vaccine can likewise be administered to a non-mammal subject, for example, a chicken, to elicit an immune response.

The vaccine dose can be between 1 microgram and 10 mg active component per kilogram (kg) body weight over time (component/kg body weight/time), and can be 20 micrograms to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

Methods of Generating an Immune Response with the Vaccine

The vaccine can be used to generate an immune response in a mammal or non-mammal subject, including therapeutic or prophylactic immune response. The immune response can generate antibodies and/or killer T cells which are directed to the one or more cancer antigens as disclosed herein. Such antibodies and T cells can be isolated.

Some embodiments provide methods of generating immune responses against one or more of the cancer antigens as disclosed herein, which embodiments comprise administering the vaccine to a subject. Some embodiments provide methods of prophylactically vaccinating a subject against a cancer or tumor expressing one or more of the cancer antigens as described above, which embodiments comprise administering the vaccine. Some embodiments provide methods of therapeutically vaccinating a subject that has been suffering from the cancer or tumor expressing one or more of the cancer antigens, which embodiments comprise administering the vaccine. Diagnosis of the cancer or tumor expressing the one or more cancer antigens as disclosed herein prior to administration of the vaccine can be done routinely.

Methods of Cancer Treatment with the Vaccine

The vaccine can be used to generate or elicit an immune response in a mammal or subject in need thereof that is reactive or directed to an HPV-mediated PRAME-expressing cancer such as but not limited to ovarian cancer, and specifically, epithelial ovarian cancer. The elicited immune response can prevent cancer or tumor growth. The elicited immune response can prevent and/or reduce metastasis of cancerous or tumor cells. Accordingly, the vaccine can be used in a method that treats and/or prevents cancer or tumors in the mammal or subject administered the vaccine.

In some embodiments, the administered vaccine can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as CD8$^+$ (CTL) to attack and kill tumor cells; (3) increase T helper cell responses; (4) and increase inflammatory responses via IFN-γ and TFN-α or preferably all of the aforementioned.

In some embodiments, the immune response can generate a humoral immune response and/or an antigen-specific cytotoxic T lymphocyte (CTL) response that does not cause damage to or inflammation of various tissues or systems (e.g., brain or neurological system, etc.) in the subject administered the vaccine.

In some embodiments, the administered vaccine can increase tumor free survival, reduce tumor mass, or a combination thereof in the subject. The administered vaccine can increase tumor free survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject. The administered vaccine can reduce tumor mass by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% in the subject after immunization. The administered vaccine can prevent and block PRAME-mediated inhibition of retinoic acid receptor.

In some embodiments, the vaccine can be administered to the periphery (as described in more detail below) to establish an antigen-specific immune response targeting the cancerous or tumor cells or tissue to clear or eliminate the cancer or tumor expressing the one or more cancer antigens without damaging or causing illness or death in the subject administered the vaccine.

The administered vaccine can increase a cellular immune response in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase the cellular immune response in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The administered vaccine can increase interferon gamma (IFN-γ) levels in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase IFN-γ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The vaccine dose can be between 1 microgram and 10 mg active component per kilogram (kg) body weight over time (component/kg body weight/time), and can be 20 micrograms to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

Routes of Administration

The vaccine or pharmaceutical composition can be administered by different routes including orally, parenterally, sublingually, transdermally, rectally, transmucosally, topically, via inhalation, via buccal administration, intrapleurally, intravenously, intraarterially, intraperitoneally, subcutaneously, intramuscularly, intranasal intrathecally, and/or intraarticularly, or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gene guns", or other physical methods such as electroporation ("EP"), "hydrodynamic method", or ultrasound.

The vector of the vaccine can be administered to the mammal by several well-known technologies including DNA injection (also referred to as DNA vaccination) with and without in vivo electroporation, liposome mediated transfection, nanoparticle facilitated transfection, and use recombinant vectors such as recombinant adenovirus, recombinant adenovirus associated virus, and recombinant vaccinia. The one or more cancer antigens of the vaccine can be administered via DNA injection along with in vivo electroporation.

Electroporation

The vaccine or pharmaceutical composition can be administered by electroporation. Administration of the vaccine via electroporation can be accomplished using electroporation devices that can be configured to deliver to a desired tissue of a mammal a pulse of energy effective to cause reversible pores to form in cell membranes, and preferably the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, Pa.) or Elgen electroporator (Inovio Pharmaceuticals, Inc.) to facilitate transfection of cells by the plasmid.

Examples of electroporation devices and electroporation methods that can facilitate administration of the DNA vaccines of the present invention include those described in U.S. Pat. No. 7,245,963; U.S. Publication No. 2005/0052630, the contents of which are hereby incorporated by reference in their entirety. Other electroporation devices and electroporation methods that can be used for facilitating administration of the DNA vaccines include those provided in co-pending and co-owned U.S. patent application Ser. No. 11/874,072, filed Oct. 17, 2007, U.S. Applications Nos. 60/852,149, filed Oct. 17, 2006, and 60/978,982, filed Oct. 10, 2007, all of which are hereby incorporated in their entirety.

U.S. Pat. No. 7,245,963 describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then administering via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference in its entirety.

U.S. Publication No. 2005/0052630 describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Publication No. 2005/0052630 is hereby fully incorporated by reference.

The electrode arrays and methods described in U.S. Pat. No. 7,245,963 and U.S. Publication No. 2005/0052630 can be adapted for deep penetration into not only tissues such as muscle, but also other tissues or organs. Because of the configuration of the electrode array, the injection needle is also inserted completely into the target organ, and the injection is administered perpendicular to the target issue, in the area that is pre-delineated by the electrodes. The electrodes described in U.S. Pat. No. 7,245,963 and U.S. Publication No. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525, issued Dec. 28, 1993; U.S. Pat. No. 6,110,161, issued Aug. 29, 2000; U.S. Pat. No. 6,261,281, issued Jul. 17, 2001; U.S. Pat. No. 6,958,060, issued Oct. 25, 2005; and U.S. Pat. No. 6,939,862, issued Sep. 6, 2005. Furthermore, patents covering subject matter provided in U.S. Pat. No. 6,697,669, issued Feb. 24, 2004, which concerns administration of DNA using any of a variety of devices, and U.S. Pat. No. 7,328,064 issued Feb. 5, 2008, drawn to methods of injecting DNA are contemplated herein. The above-patents are incorporated by reference in their entirety.

Methods of Preparing the Vaccine

Provided herein are methods for preparing the vectors included in the vaccines discussed herein. The vectors, after the final subcloning step, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a U.S. Publication No. 2009/0004716, filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Application No. 60/939,792, including those described in a licensed patent, U.S. Pat. No. 7,238,522, issued on Jul. 3, 2007. The above-referenced application and patent, U.S. Application No. 60/939,792 and U.S. Pat. No. 7,238,522, respectively, are hereby incorporated in their entirety.

The present invention has multiple aspects, illustrated by the following non-limiting examples.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Synthetic Consensus PRAME

In order to generate a human consensus PRAME, 10 PRAME sequences were collected from GenBank (https://www.ncbi.nlm.nih.gov/genbank/). The GenBank accession numbers for selected PRAME sequences are:
NP_006106.1, AFX65483.1, XP_001090516.1, AFI35054.1, AFJ71405.1, XP_003805956.1, XP_525643.2, BAK62424.1, XP_003919211.1, and XP_003919212.1.

A consensus sequence was generated using the DNASTAR® Lasergene software package (version 13.0.0.357). The sequences listed above were imported into MegAlign and aligned using the ClustalW multiple sequence alignment program. The resulting PRAME sequence shares 95.1%-95.5% homology with the native human PRAME sequences.

Once the synthetic consensus PRAME DNA sequence was obtained, in order to have a higher level of expression an upstream Kozak sequence and IgE leader were added to the N-terminus. Furthermore, the codon usage of this gene was adapted to the codon bias of *Homo sapiens* genes. Additionally, RNA optimization was performed: regions of very high (>80%) or very low (<30%) GC content and the cis-acting sequence motifs such as internal TATA boxes, chi-sites and ribosomal entry sites were avoided. To eliminate the potential function of an expressed PRAME molecule in retinoic acid signaling repression, two point mutations were introduced (L487V and L488V) in the nuclear receptor box LRELL (SEQ ID NO: 4) of PRAME, resulting in a modified synthetic consensus PRAME. This modified synthetic consensus PRAME protein sequence shares 94.7%-95.1% identity with human native PRAME proteins. Characteristics of the synthetic consensus PRAME are provided in Table 1.

TABLE 1

Characteristics of Synthetic Consensus PRAME

| Characteristics | Modified Synthetic Consensus PRAME |
|---|---|
| Identity to native human PRAME | 94.7%-95.1% |
| Identity to native rhesus PRAME | 98.6% |

TABLE 1-continued

Characteristics of Synthetic Consensus PRAME

| Characteristics | Modified Synthetic Consensus PRAME |
|---|---|
| Identity to native mouse PRAME | 35.2% |
| Number of amino acid mutations (vs native human) | 25-27 |
| Number of inserted mutations (not consensus derived) | 2 |
| Molecular weight | 528 aa (58 kDa) |
| Length of coding sequence (bp) | 1584 |

Figure 2:
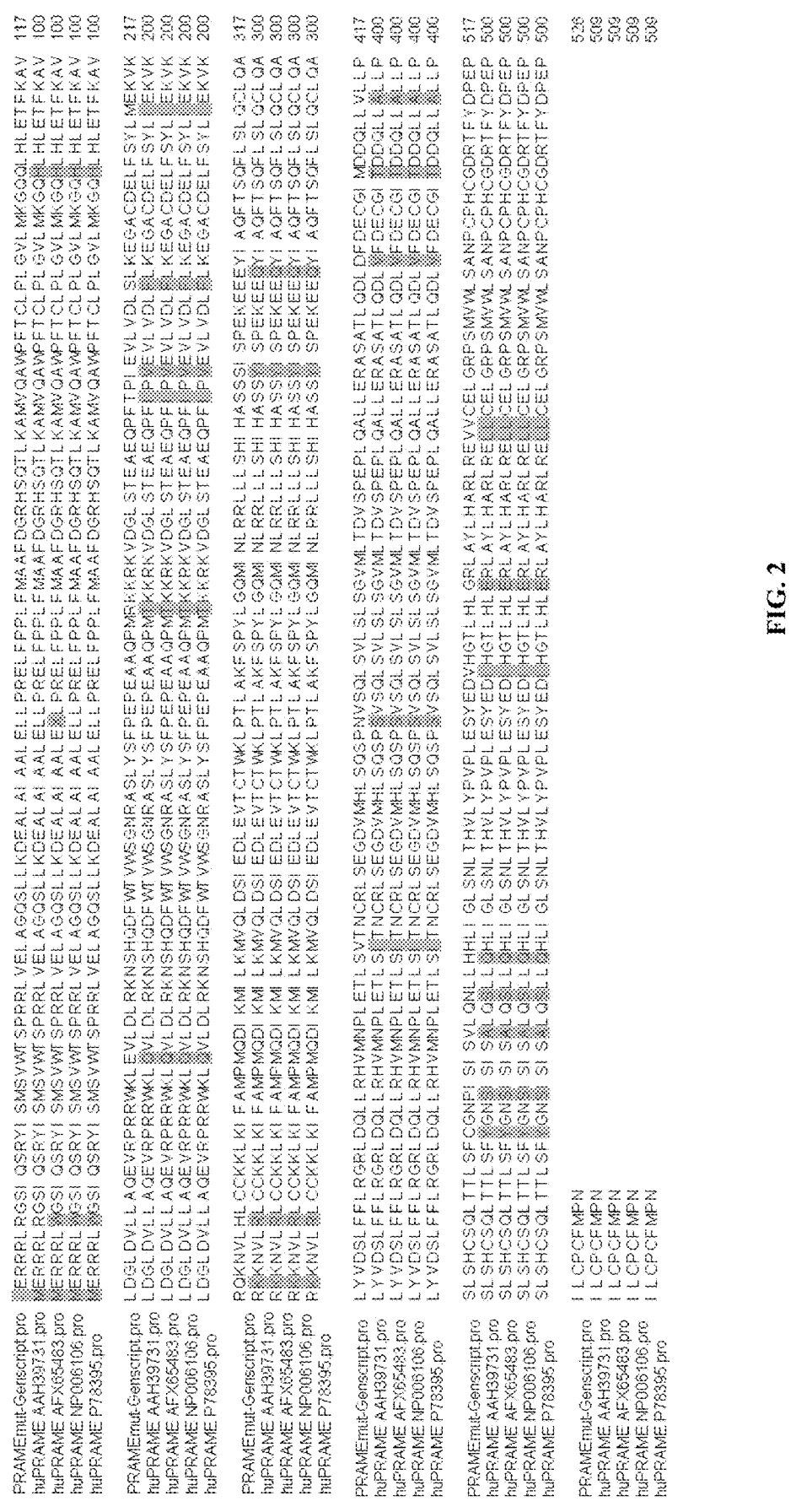

Referring to FIG. 2, a sequence alignment of the modified consensus PRAME with five human PRAME sequences illustrates the amino acid differences between the sequences. The leucine to valine substitutions at amino acid residues 487 and 488 of the modified synthetic consensus PRAME are among the highlighted amino acid differences. Percent identities between the aligned sequences are presented in Table 2.

TABLE 2

Percent Identity of Modified Consensus PRAME with human PRAME

|   | 1 | 2 | 3 | 4 | 5 |   |
|---|---|---|---|---|---|---|
| 1 |   | 95.1 | 94.7 | 94.9 | 94.9 | PRAMEmut-GenScript.pro |
| 2 | 5.1 |   | 99.6 | 99.8 | 99.8 | huPRAME(AAH39731.pro) |
| 3 | 5.5 | 0.4 |   | 99.8 | 99.8 | huPRAME(AFX65483).pro |
| 4 | 5.3 | 0.2 | 0.2 |   | 100 | huPRAME(NP_006106).pro |
| 5 | 5.3 | 0.2 | 0.2 | 0.0 |   | huPRAME(78395).pro |

Comparisons of unmodified synthetic consensus PRAME and modified consensus PRAME are provided in Table 3.

TABLE 3

Comparison of Modified and Unmodified Consensus PRAME

|   | Human Sequence | Mouse Sequence | Macaque Sequence |
|---|---|---|---|
| Consensus PRAME | 95.1% to 95.5% | 39.8% to 42.6% | 98.6% to 98.8% |
| Modified Consensus PRAME | 94.7% to 95.1% | 39.8% to 42.1% | 98.4% to 98.6% |

Figure 3:
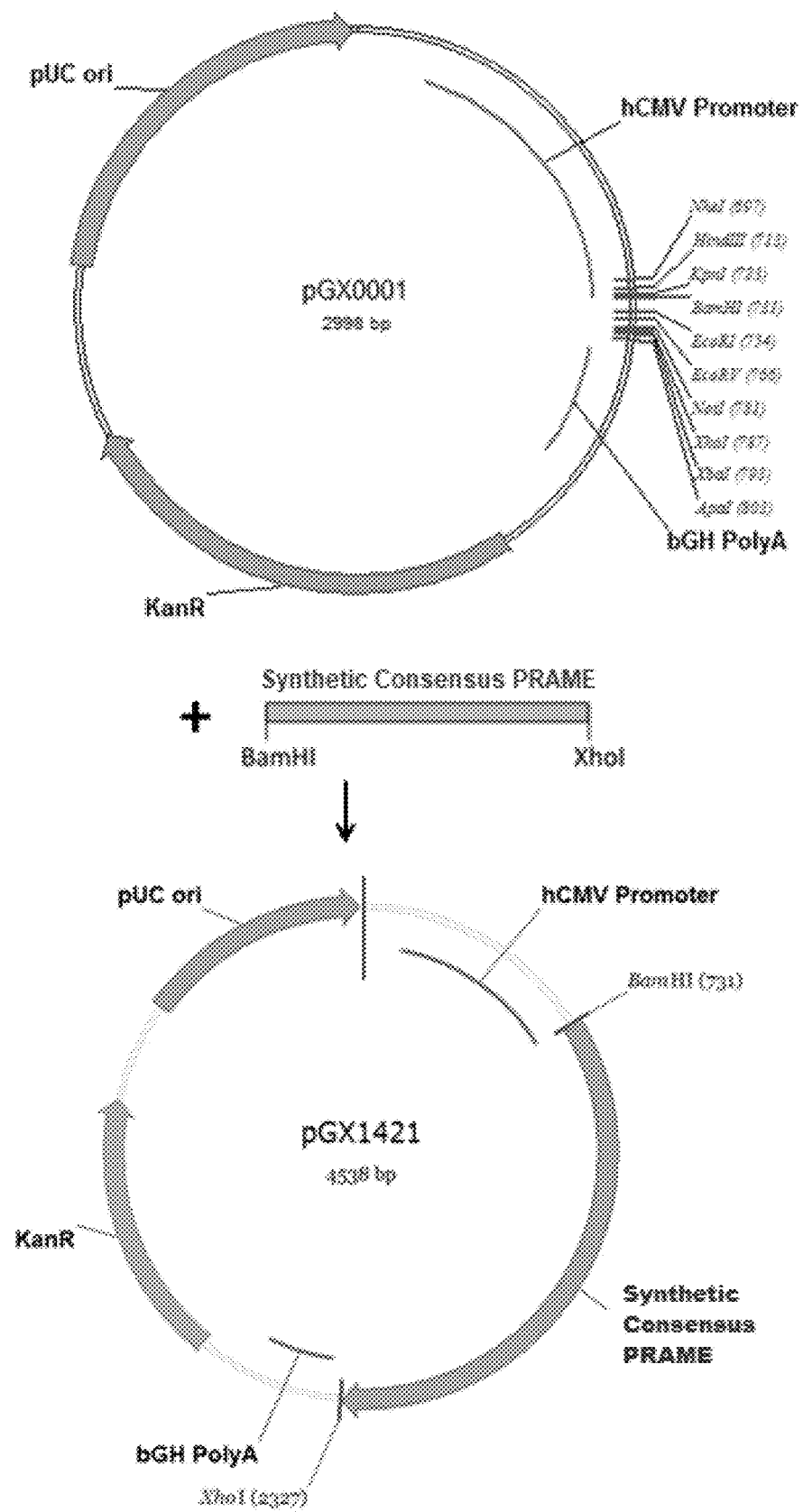
FIG. 3 generally depicts the cloning reaction that yields pGX1421.

Referring to FIG. 3, the synthesized synthetic consensus PRAME was digested with BamHI and XhoI, and cloned into Inovio's expression vector pGX0001 with the expression cassette placed under the transcriptional control of the cytomegalovirus immediate-early promoter. The resulting plasmid was designated pGX1421 and full length sequencing was performed to confirm the sequence.

pGX1421 is a DNA plasmid encoding the synthetic consensus PRAME protein. Related mRNA production is driven by a human CMV promoter (hCMV promoter) and terminated by the bovine growth hormone 3'-end polyadenylation signal (bGH polyA). The pGX0001 backbone (a modified pVAX1 expression vector, the original pVAX1 was obtained from ThermoFisher, St. Louis, Mo.) includes the kanamycin resistance gene (KanR) and plasmid origin of replication (pUC ori) for production purpose. Those elements are not functional in eukaryotic cells.

Modifications were introduced into pVAX1 to create pGX0001 and are identified based on the reported sequence of pVAX1 available from ThermoFisher Scientific. These modifications are listed below and no issues were detected regarding plasmid amplification and antigen transcription and translation.

C>G 241 in CMV promoter

C>T 1158 backbone, downstream of the bovine growth hormone polyadenylation signal (bGH polyA)

A>-2092 backbone, downstream of the Kanamycin resistance gene

C>T 2493 in pUC origin of replication (pUC ori)

G>C 2969 in very end of pUC Ori upstream of RNASeH site

Base pairs 2, 3 and 4 are changed from ACT to CTG in backbone, upstream of CMV promoter.

Example 2

PRAME Expression

Figure 4:
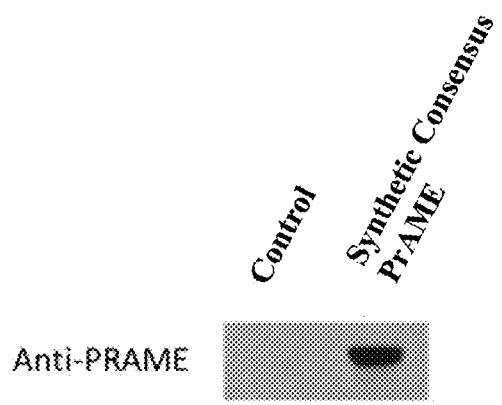
FIG. 4 illustrates confirmation by Western blot analysis of expression of PRAME antigen in cell lines transfected with the synthetic consensus PRAME.
Figure 5:
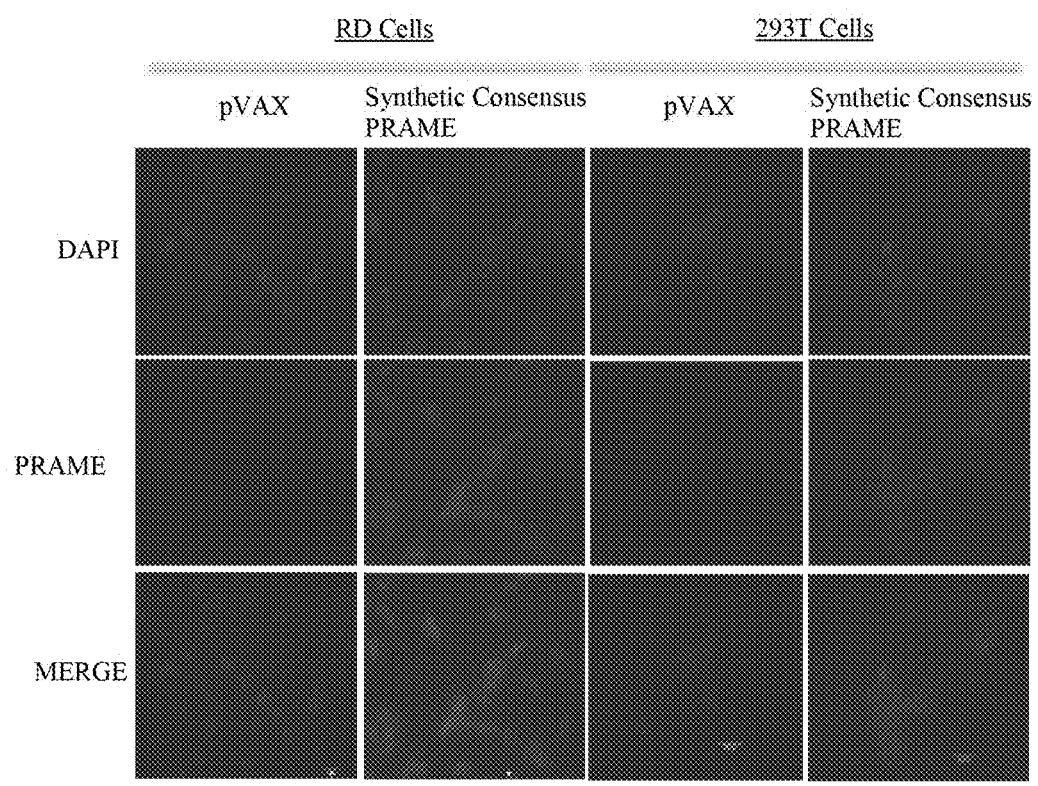
FIG. 5 depicts results of an immunoassay comparing expression of synthetic consensus PRAME to a control (pVAX).

PRAME expression was examined in cell lines transfected with a plasmid encoding the synthetic consensus PRAME (pGX1411) or a control to determine if the synthetic antigen was expressed. Western blot analysis of the cell lines using a commercially available anti-PRAME antibody and a β-Actin control antibody shows that only those cells transfected with pGX1411 exhibited expression of PRAME protein that migrated at the correct molecular weight (FIG. 4). An indirect immunofluorescent assay compared PRAME gene expression to pVAX expression in Rhabdomyosarcoma cells and Hek293 cells. Referring to FIG. 5, the synthetic consensus PRAME was expressed in both cell lines while the pVAX negative control was not.

Example 3

Immunogenicity in Mice

Figure 6:
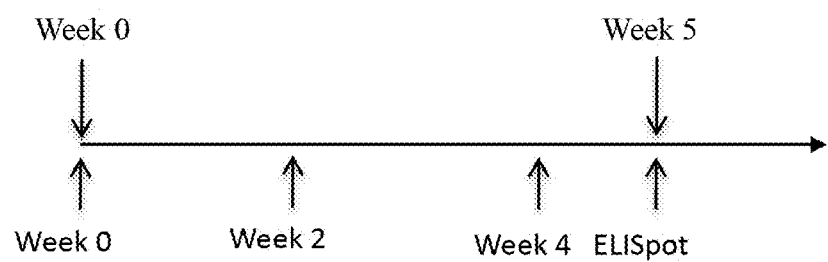
FIG. 6 depicts the immunization and bleed schedules for an immunogenicity study performed in C57Bl/6 mice.
Figure 7:
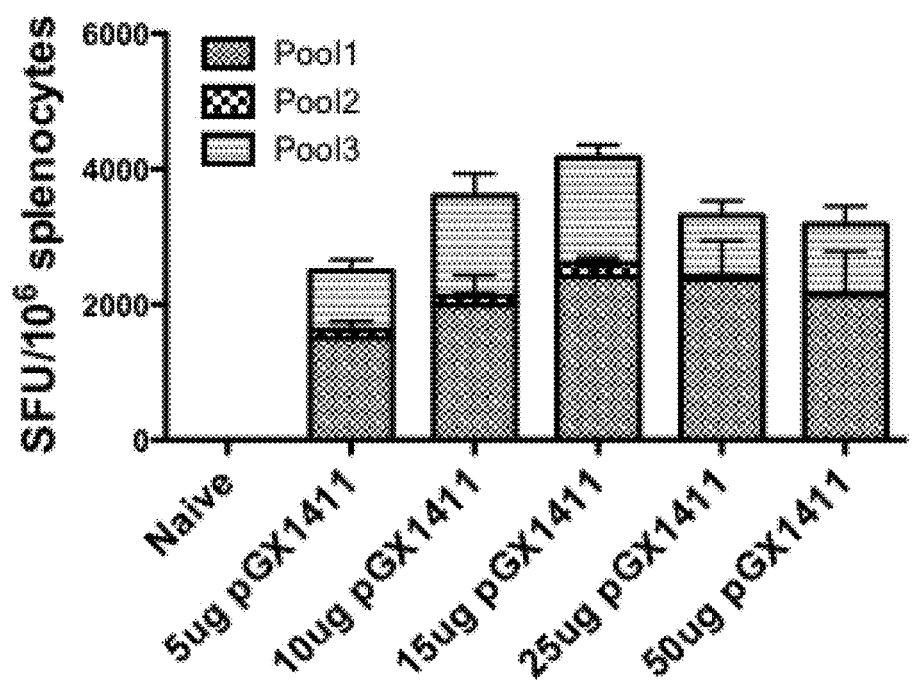
FIG. 7 depicts the dose response of pGX1411 in mice.

Immunogenicity studies were performed in C57Bl/6 mice according to the immunization and bleed schedule depicted in FIG. 6. Briefly, dosages of 5, 10, 15, 25, and 50 μg of pGX1411 per immunization were administered to mice at time points Week 0 (initial immunization), Week 2, Week 4, and ELISpot. Mice were bled at time points Week 0 (baseline measurement) and Week 5. A dose response study was initially performed to determine the most effective dose, and, referring to FIG. 7, all doses investigated resulted in a greater response than naïve. There was a slight increase in response with increasing dose up to 15 μg pGX1411 DNA. At higher doses of 25 and 50 μg of pGX1411 DNA, the response plateaued.

Figure 8A:
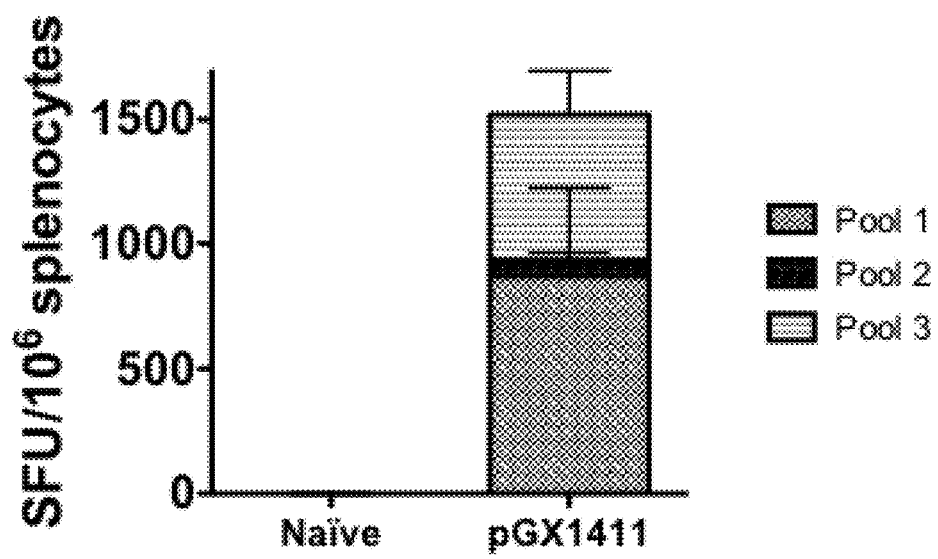
FIG. 8A illustrates confirmation that pGX1411 is immunogenic in mice.
Figure 8B:
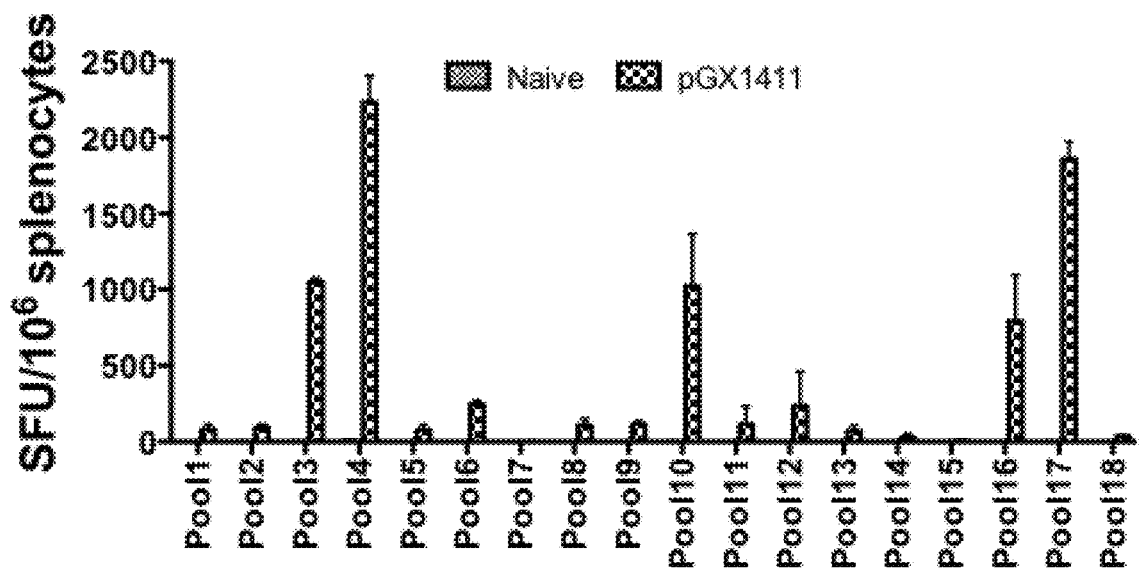
FIG. 8B graphically depicts the immune response in mice after administration of pGX1411 or untreated mice.

The synthetic consensus PRAME was highly immunogenic (FIG. 8A) in mice and immunodominant epitopes were identified by epitope mapping (FIG. 8B and Table 4). In brief, peptides spanning the entire consensus PRAME, each containing 15 amino acid residues overlapping by 8 amino acids were produced. These peptides were pooled into 3 peptide pools (Table 4). Splenocytes from naïve and pGX1411 immunized mice were stimulated with the 3 peptide pools in mouse IFNγ ELISpot assays. The results are shown in FIG. 8A. Immunodominant epitopes were identified using a peptide matrix mapping approach (FIG. 8B). Immunodominant epitopes are underlined in Table 4.

TAGLE 4

Immunodominant epitopes identified in mice immunized with pGX1411

| Pool Number | No. of Epitope-Comprising Peptides | Sequence of Epitope-Comprising Peptides |
|---|---|---|
| Pool 1 aa 1-197 | 22 Peptides | RVHSERRRLRGSIQS (SEQ ID NO: 5)<br>RLRGSIQSRYISMSV (SEQ ID NO: 6)<br>SRYISMSVWTSPRRL (SEQ ID NO: 7)<br>VWTSPRRLVELAGQS (SEQ ID NO: 8)<br>LVELAGQSLLKDEAL (SEQ ID NO: 9)<br>SLLKDEALAIAALEL (SEQ ID NO: 10)<br>LLPRELFPPLFMAAF (SEQ ID NO: 11)<br>PPLFMAAFDGRHSQT (SEQ ID NO: 12)<br>FDGRHSQTLKAMVQA (SEQ ID NO: 13)<br>TLKAMVQAWPFTCLP (SEQ ID NO: 14)<br>AWPFTCLPLGVLMKG (SEQ ID NO: 15)<br>PLGVLMKGQQLHLET (SEQ ID NO: 16)<br>GQQLHLETFKAVLDG (SEQ ID NO: 17)<br>TFKAVLDGLDVLLAQ (SEQ ID NO: 18)<br>GLDVLLAQEVRPRRW (SEQ ID NO: 19)<br>QEVRPRRWKLEVLDL (SEQ ID NO: 20)<br>WKLEVLDLRKNSHQD (SEQ ID NO: 21)<br>LRKNSHQDFWTVWSG (SEQ ID NO: 22)<br>DFWTVWSGNRASLYS (SEQ ID NO: 23)<br>GNRASLYSFPEPEAA (SEQ ID NO: 24)<br>SFPEPEAAQPMRKKR (SEQ ID NO: 25)<br>AQPMRKKRKVDGLST (SEQ ID NO: 26)<br>RKVDGLSTEAEQPFT (SEQ ID NO: 27) |
| Pool 2 aa 190-372 | 10 Peptides | TPIEVLVDLSLKEGA (SEQ ID NO: 28)<br>DLSLKEGACDELFSY (SEQ ID NO: 29)<br>ACDELFSYLMEKVKR (SEQ ID NO: 30)<br>YLMEKVKRQKNVLHL (SEQ ID NO: 31)<br>RQKNVLHLCCKKLKI (SEQ ID NO: 32)<br>LCCKKLKIFAMPMQD (SEQ ID NO: 33)<br>IFAMPMQDIKMILKM (SEQ ID NO: 34)<br>DIKMILKMVQLDSIE (SEQ ID NO: 35)<br>EDLEVTCTWKLPTLA (SEQ ID NO: 36)<br>TWKLPTLAKFSPYLG (SEQ ID NO: 37) |
| Pool 3 aa 365-526 | 15 Peptides | ASATLQDLDFDECGI (SEQ ID NO: 38)<br>LDFDECGIMDDQLLV (SEQ ID NO: 39)<br>IMDDQLLVLLPSLSH (SEQ ID NO: 40)<br>VLLPSLSHCSQLTTL (SEQ ID NO: 41)<br>HCSQLTTLSFCGNPI (SEQ ID NO: 42)<br>LSFCGNPISISVLQN (SEQ ID NO: 43)<br>NLLHHLIGLSNLTHV (SEQ ID NO: 44)<br>GLSNLTHVLYPVPLE (SEQ ID NO: 45)<br>ESYEDVHGTLHLGRL (SEQ ID NO: 46)<br>GTLHLGRLAYLHARL (SEQ ID NO: 47)<br>LAYLHARLRELLCEL (SEQ ID NO: 48)<br>LRELLCELGRPSMVW (SEQ ID NO: 49)<br>LGRPSMVWLSANPCP (SEQ ID NO: 50)<br>PHCGDRTFYDPEPIL (SEQ ID NO: 51)<br>FYDPEPILCPCFMPN (SEQ ID NO: 52) |

(Previously published HLA-A*02-restricted PRAME peptides: ALYVDSLFFL (SEQ ID NO: 53), VLDGLDVLL (SEQ ID NO: 54), SLYSFPEA (SEQ ID NO: 55), SLLQHILGL (SEQ ID NO: 56) and NLTHVLYPV (SEQ ID NO: 57) (Quintarelli et al. 2011)).

Figure 9A:
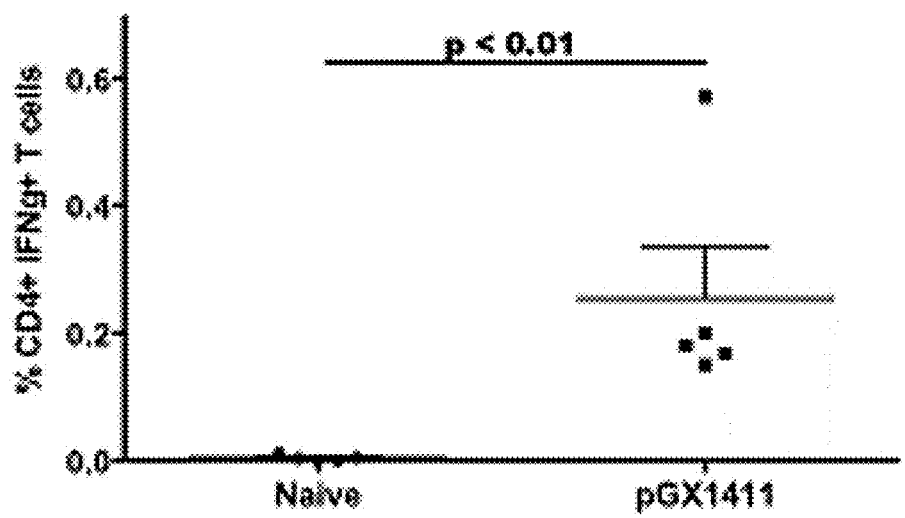
FIGS. 9A-9F graphically depict the results of flow cytometry analysis to determine the CD4+ and CD8+ T-cell responses in mice. Specifically.
Figure 9B:
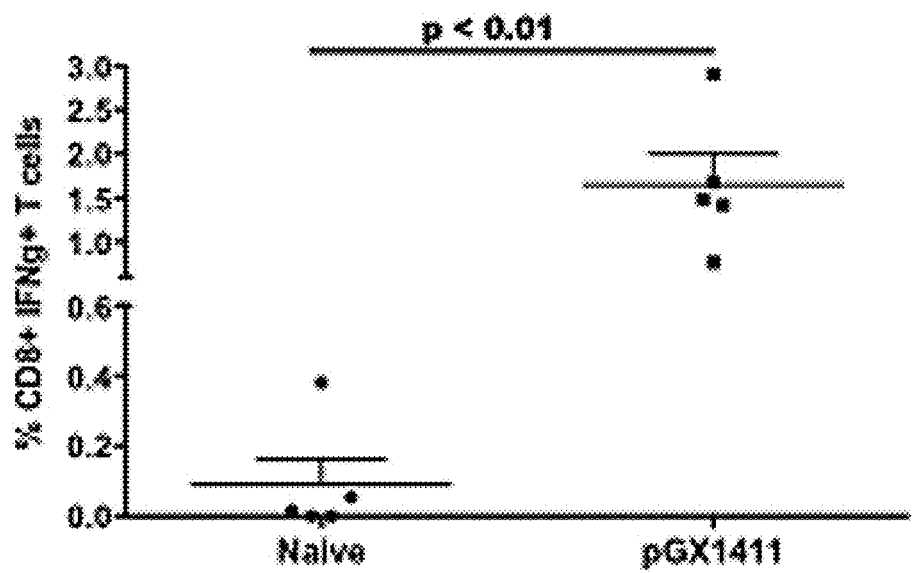
Figure 9C:
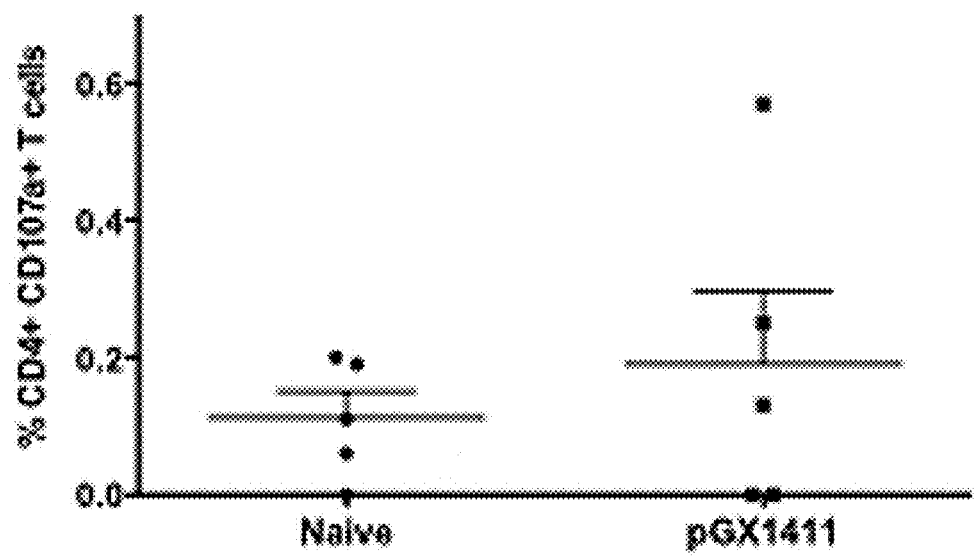
Figure 9D:
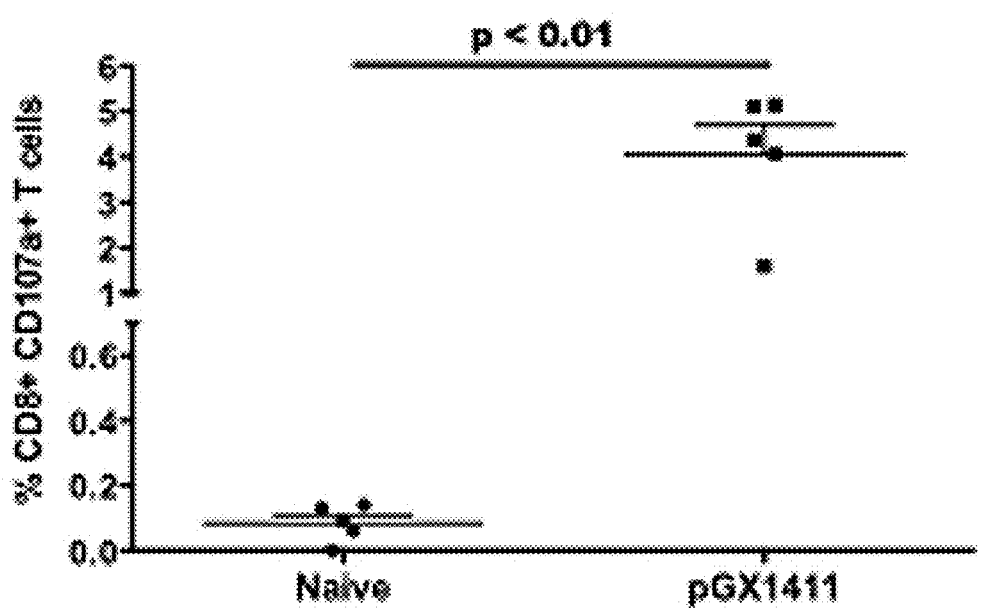
Figure 9E:
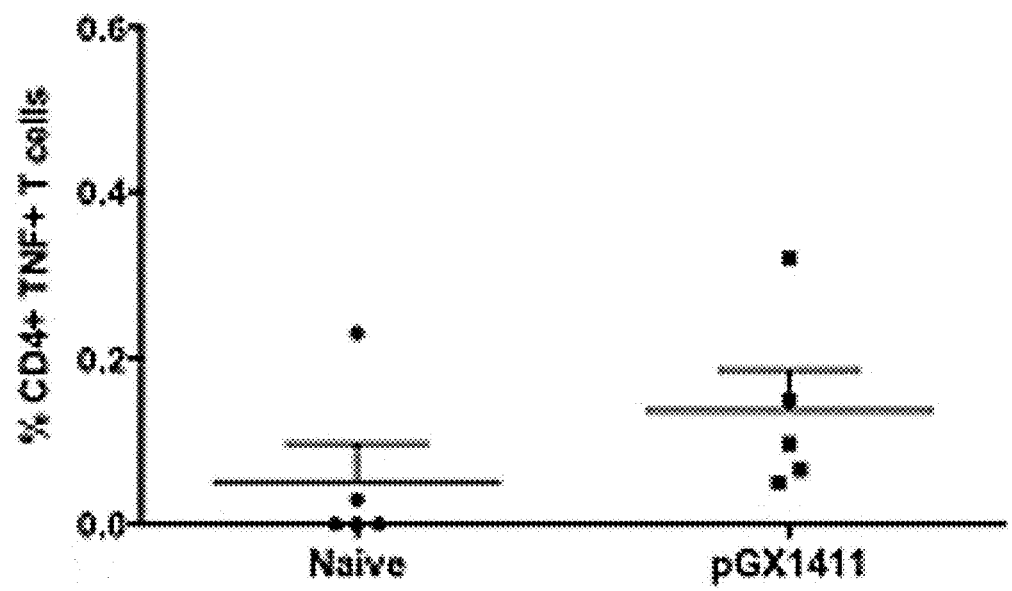
Figure 9F:
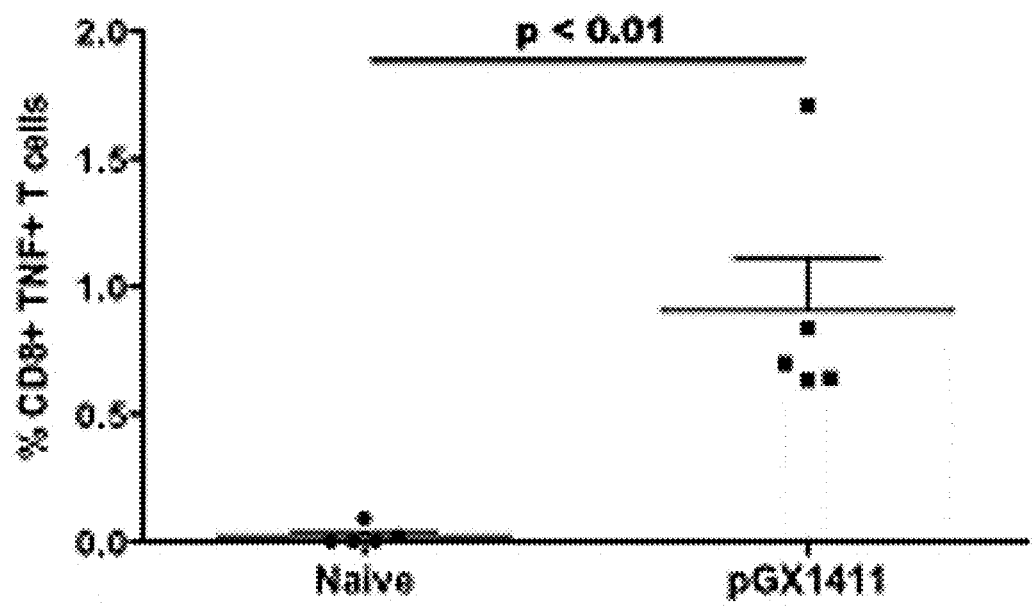

Antigen-specific CD4+ and CD8+ T cell responses induced by pGX1411 were assessed by intracellular cytokine staining of peptide stimulated splenocytes from naïve and pGX1411 treated mice. CD4+ cells from pGX1411 treated mice showed a small although significant increase in IFN-γ after treatment with pGX1411 (FIG. 9A), whereas CD8+ cells resulted in an almost 10-fold greater significant increase (FIG. 9B). For TNF-α and CD107a+, CD8+ cells resulted in a significantly greater increase with pGX1411 treatment (FIGS. 9D and 9F), whereas for CD4+ cells there was no difference between naïve and pGX1411 treatment (FIGS. 9C and 9E). Overall, the synthetic consensus PRAME induces both CD4+ and CD8+ T-cells, with CD8+ showing a higher cytokine response.

Figure 10:
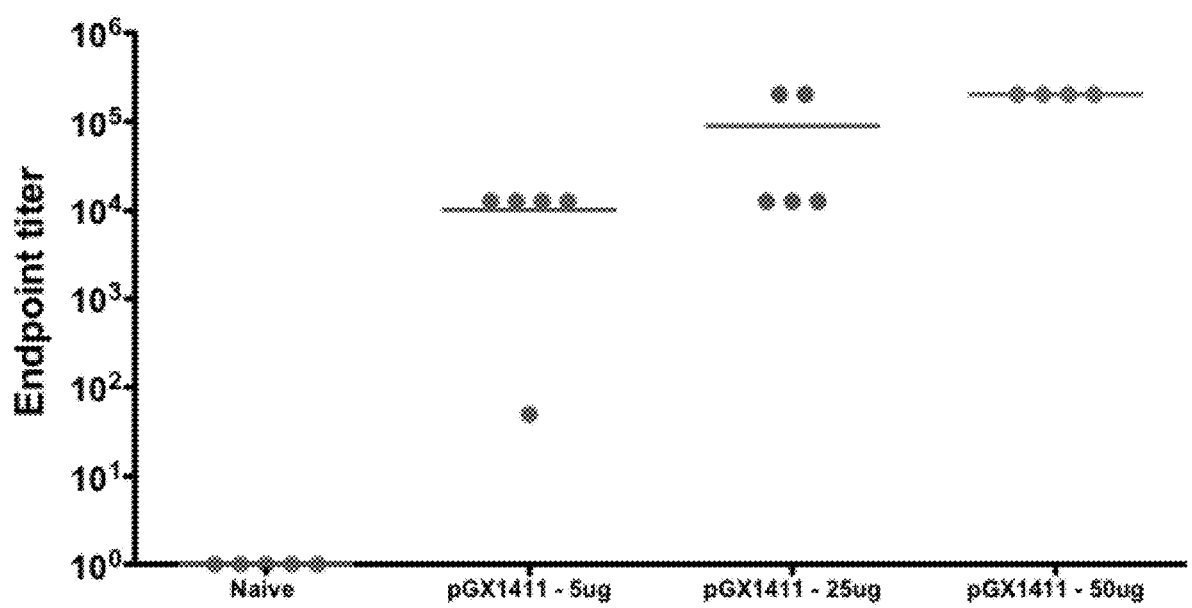
FIG. 10 graphically depicts endpoint titers after treatment with 5, 25, and 50 μg of pGX1411 compared to untreated controls.
Figure 11:
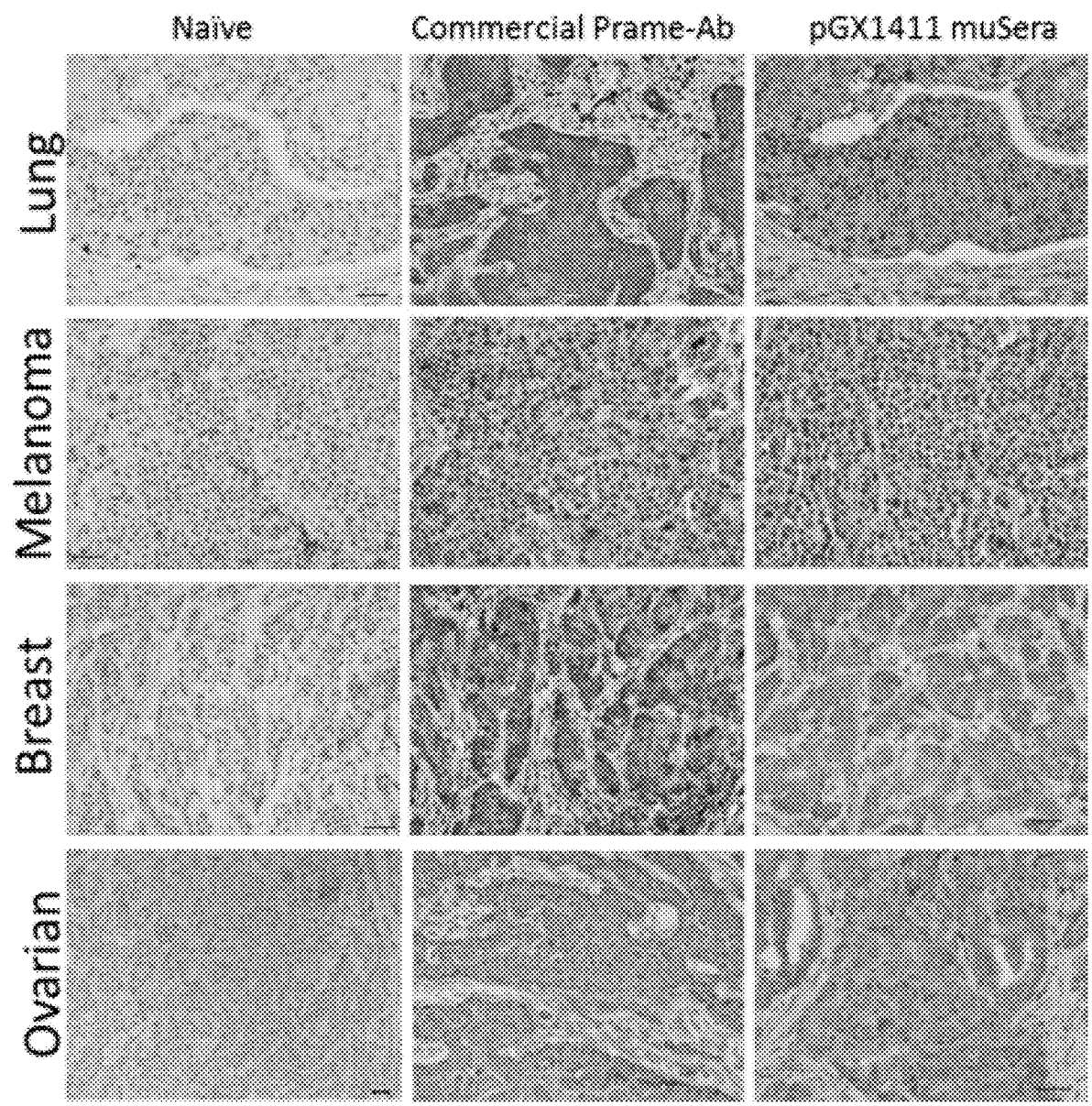
FIG. 11 presents immunohistochemistry staining of cancerous tissue.

Endpoint titers were determined in a dose response manner for pGX1411, namely 5, 25, and 50 µg, as shown in FIG. 10. Each dose examined increased the endpoint titer compared to naïve, although increasing dose did not significantly increase the endpoint titer response. To determine whether pGX1411-induced antibodies could recognize native PRAME expressed in human cancers the reactivity of pGX1411 in cancer was investigated by immuno-histochemistry as shown in FIG. 11. Tissue sections from human cancer biopsies were stained with sera from naïve or pGX1411 treated mice. After treatment with biotinylated secondary antibody, tissue sections were stained with diaminobenzidine with hydrogen peroxide, and counterstained with hematoxylin. Tissue staining with a commercial PRAME antibody was used as a comparator. Positive staining was detected in the melanoma cancer tissue sample with the pGX1411 vaccinated mouse sera and the commercial PRAME antibody but not with the naïve mouse sera. Therefore, vaccination with pGX1411 has the ability to induce PRAME specific antibodies.

Figure 12:
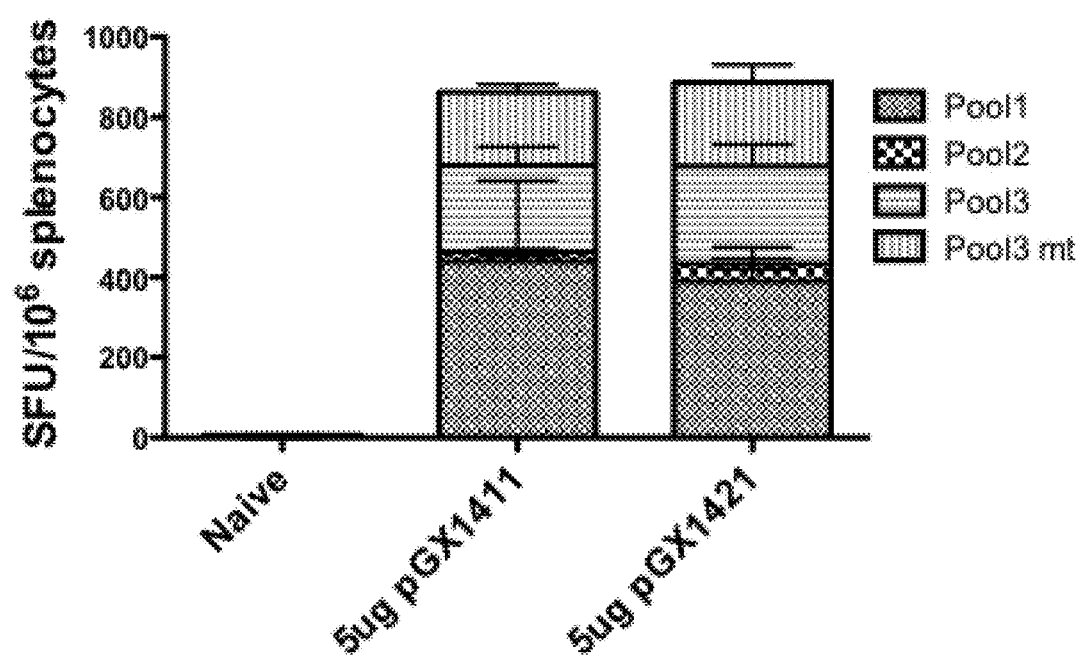
FIG. 12 graphically illustrates the comparison of immune response in mice administered synthetic consensus PRAME and modified synthetic consensus PRAME.

The modified synthetic consensus PRAME encoded by pGX1421 induces an immune response similar to that generated by the unmodified synthetic consensus PRAME encoded by pGX1411. Referring to FIG. 12, this elicited immune response by pGX1421 is comparable to that elicited by pGX1411 when investigated by ELISpot in mice. Both pGX1411 and pGX1421, at a dose of 5 µg, resulted in approximately 900 SFU/$10^6$ peripheral blood mononuclear cells (PBMCs) compared to baseline levels for naïve (0 SFU/$10^6$ PBMCs).

Example 4

Immunogenicity in Non-Human Primates (NHP)

Figure 13:
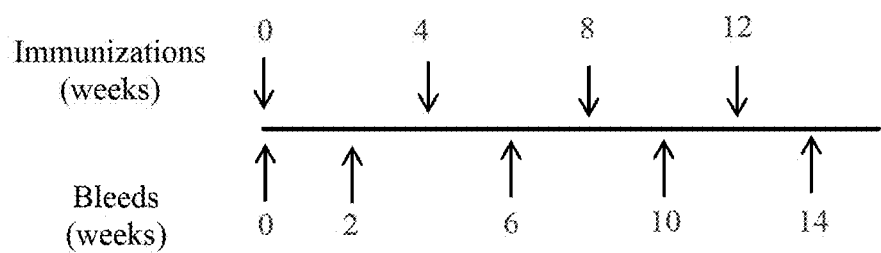
FIG. 13 illustrates the immunization and bleeding schedule for non-human primate (NHP) studies.
Figure 14A:
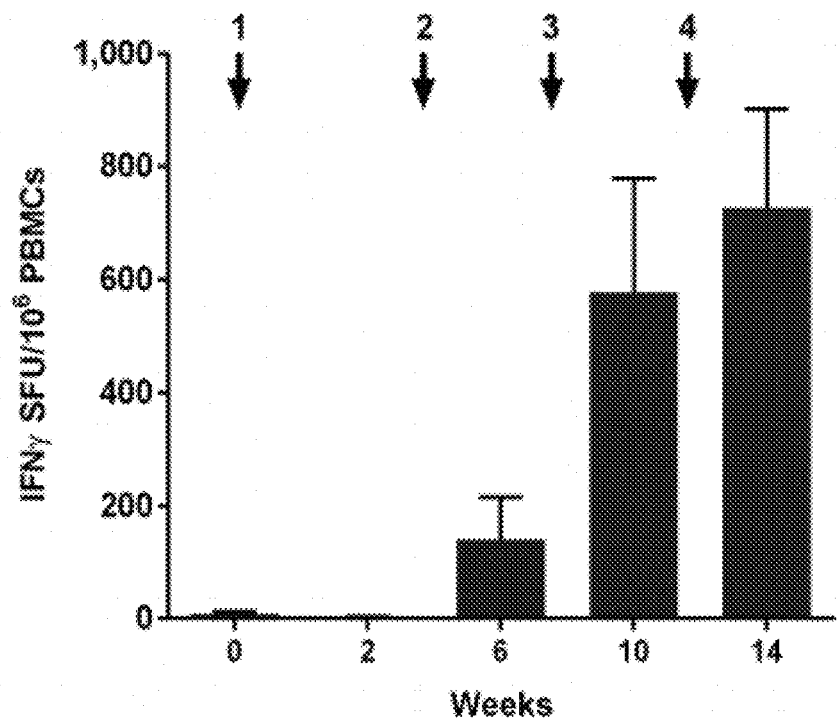
FIGS. 14A-14C depict cellular immunogenicity as determined by IFNγ ELISpot.
Figure 14B:
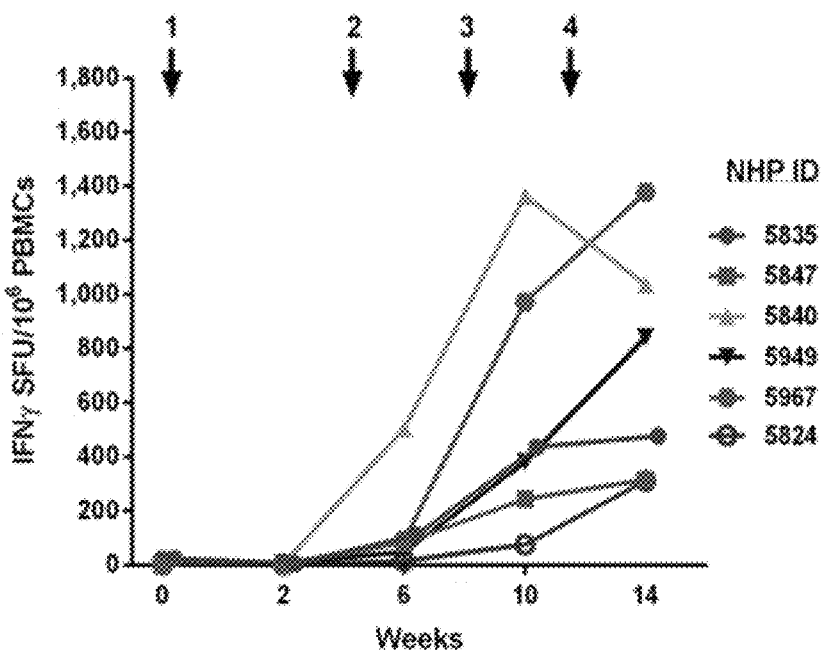
Figure 14C:
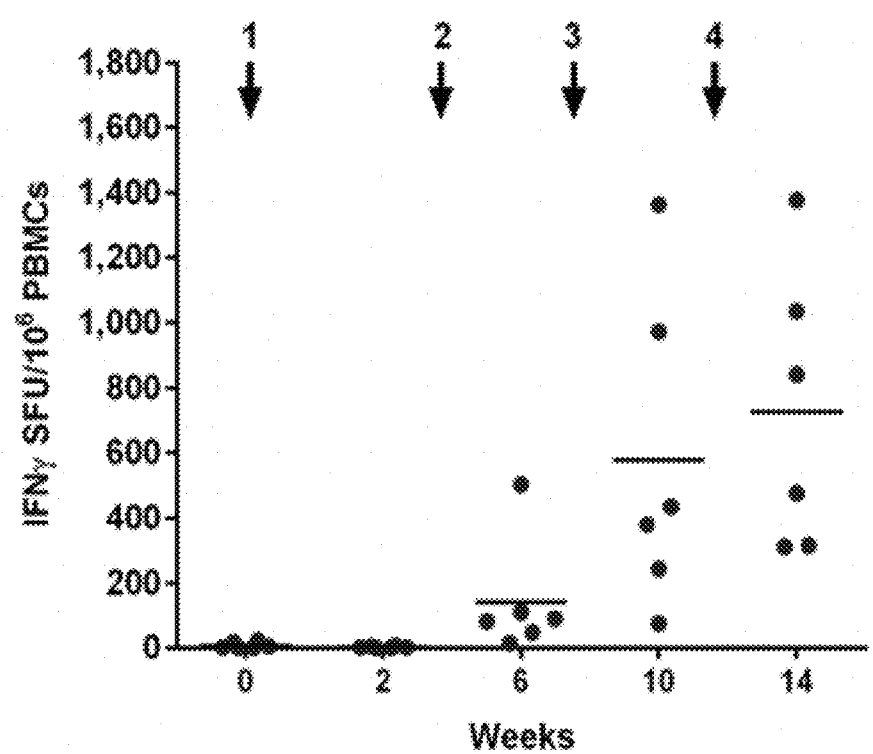

Immunogenicity studies were carried out in non-human primates (NHPs) according to the immunization and bleeding schedule depicted in FIG. 13. pGX1421 was delivered intramuscularly (IM) with the 5P CELLECTRA® in alternating contralateral limbs with optimized rhesus IL-12 (pGX6006) at week 0, 4, 8, and 12 with bleeds every 2 weeks following immunization. Referring to FIGS. 14A to 14C, cellular immunogenicity was evaluated by IFNγ ELISpot, ICS, and the measured IFNγ responses revealed an overall increase with four immunizations with pGX1421 and pGX6006. After the third immunization, IFNγ increased to approximately 600 SFU/$10^6$ PBMCs compared to baseline levels. The fourth immunization slightly boosted the response compared to the third immunization with approximately 700 SFU/$10^6$ PBMCs (FIG. 14A). The individual responses are shown in FIGS. 14B and 14C, with two out of six NHPs having greater than average response after the third immunization. This increased to three out of the six NHPs having a greater than average response after the fourth immunization. Overall, six out of six NHPs responded as determined by IFNγ ELISpot two weeks after the third immunization (week 10) compared to week 0.

Figure 15A:
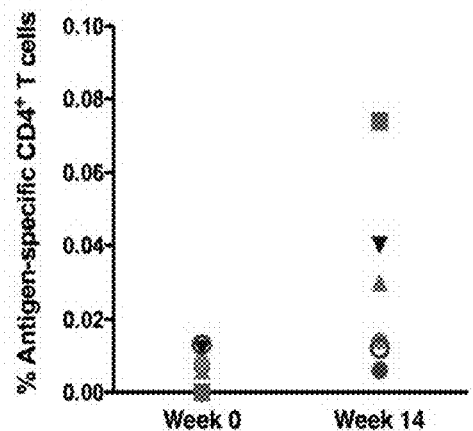
FIGS. 15A-15D illustrate the CD4+ and CD8+ T-cells responses in NHPs administered pGX1421 and PGX6006.
Figure 15B:
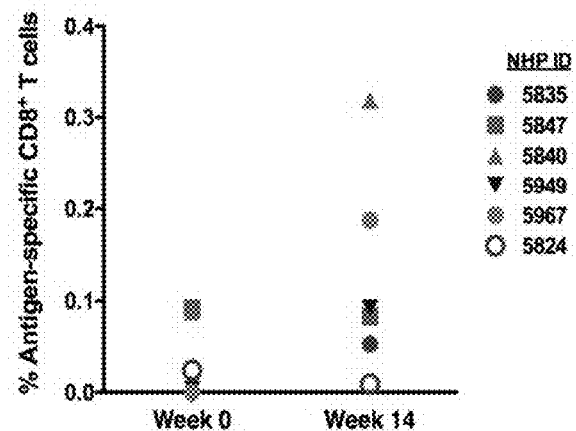
Figure 15C:
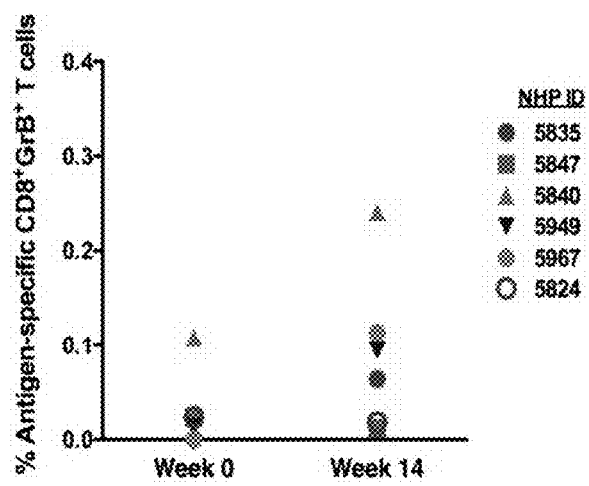
Figure 15D:
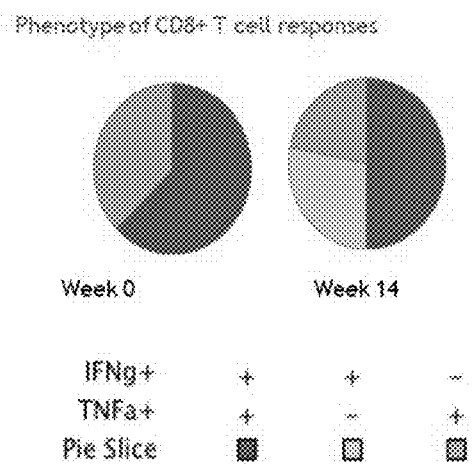

Referring to FIGS. 15A-15D, pGX1421 and pGX6006 induce minimal CD4+ T-cell responses compared to the CD8+ T-cell responses. CD4+ T cell responses were not seen in any NHP, but robust CD8+ T-cell responses were detected by ICS in the NHPs with the highest IFNγ ELISpot response two weeks after the fourth immunization, in NHP 5840 and 5967 (FIG. 15C).

Example 5

Characterizing the Adjuvant Effect of pGX6006 on PRAME-Induced Immunogenicity

Fifteen NHPs were divided into three groups as shown in Table 5 to determine the adjuvant effect of pGX6006. The immunization and bleeding schedule was the same for all three groups and is depicted in FIG. 13.

TABLE 5

Study Groups

| Group | N | Antigen Construct | Adjuvant Construct |
|---|---|---|---|
| 1 | 5 | pGX1421 (2.0 mg) | N/A |
| 2 | 5 | pGX1421 (2.0 mg) | pGX6006 (0.20 mg) |
| 3 | 5 | pGX1411 (2.0 mg) | pGX6006 (0.20 mg) |

Figures 16A, 16B, 16C:
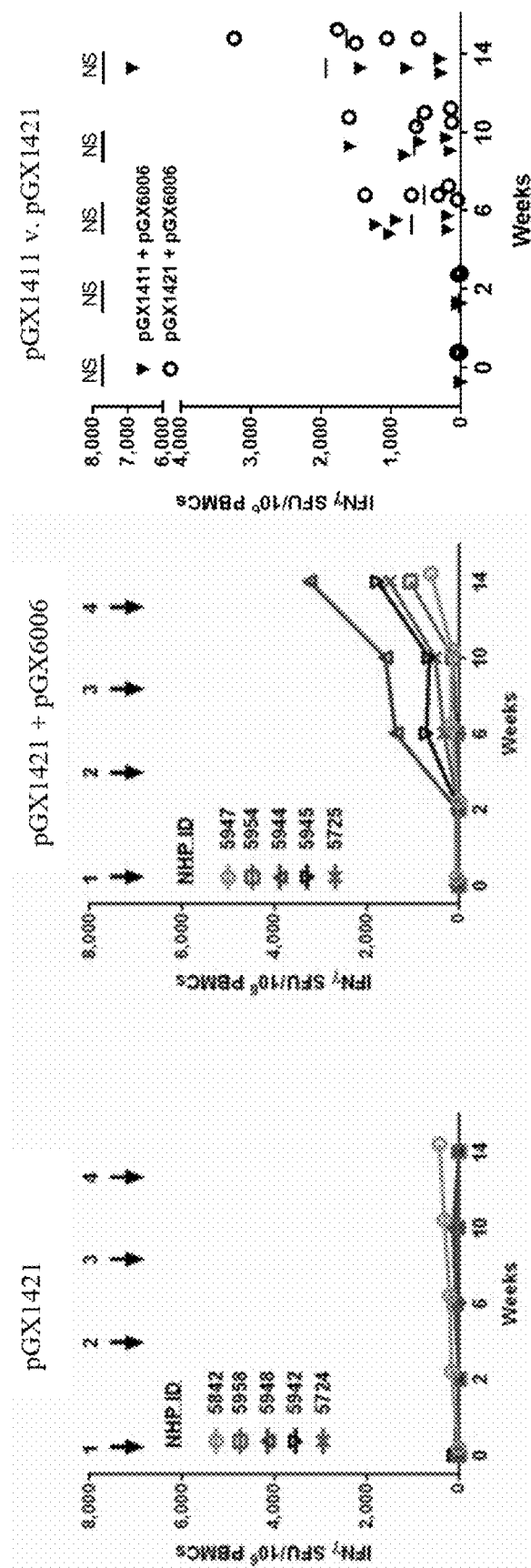
FIGS. 16A-16C illustrate the cellular immune responses induced by pGX1421 and pGX1421 in combination with pGX6006 (IL-12).

Referring to FIGS. 16A-16C, IL-12 significantly increased IFNγ responses to PRAME encoded by pGX1421 two weeks PD3 (Week 10) and PD4 (Week 14). Following the third immunization, the average IFNγ SFU induced by pGX1421 alone (108±124) was significantly lower than the average response induced by pGX1421 and pGX6006 together (609±597, p<0.08). IFNγ responses boosted in Group 2 following the fourth immunization (1636±999 SFU, p<0.08, FIG. 16C).

Cellular immune responses induced by pGX1421 and pGX1421 in combination with pGX6006 were further characterized by flow cytometry two weeks PD4 (Week 14, FIGS. 17A-17C). There were minimal responses detected in the CD4+ T-cell compartment in either group as shown in FIG. 17A. Minimal responses were detected in the CD8+ T-cell compartment when pGX1421 was administered without pGX6006 (FIG. 17B). The majority of the PRAME-specific CD8+ T-cell population detected in the pGX1421 in combination with pGX6006 group two weeks PD4 produced both IFNγ and TNFα. The remainder of the population was predominantly positive for IFNγ production alone. The majority of the antigen-specific CD8+ T-cells induced by pGX1421 in combination with pGX6006 were positive for both CD107a and Granzyme B, indicating the potential for CTL and effector function (FIG. 17C).

Figure 18A:
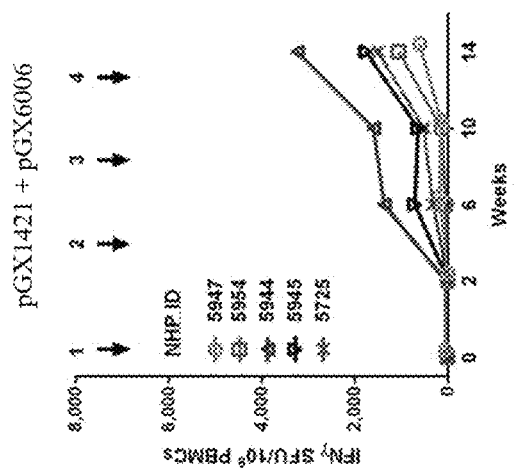
FIGS. 18A-18C compare IFNγ responses induced by administration of pGX1421 in combination with pGX6006 (FIG. 18A) to those responses induced by administration of pGX1411 in combination with pGX6006 (FIG. 18B).
Figure 18B:
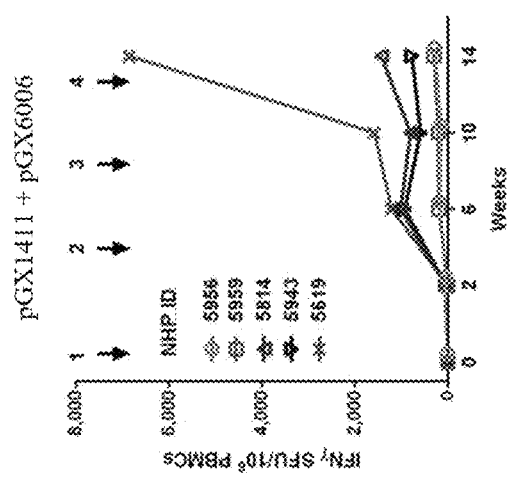
Figure 18C:
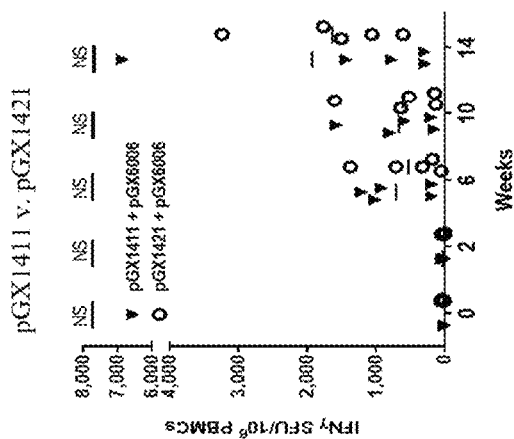

Cellular immune responses induced by pGX1411 in combination with pGX6006 and pGX1421 in combination with pGX6006 were compared by IFNγ ELISpot (FIGS. 18A-18C) and by flow cytometry two weeks PD4 (Week 14, FIG. 19A-19F). PRAME-specific IFNγ responses two weeks PD3 (666±597 SFU) and PD4 (1931±2795 SFU) induced by PGX1411 in combination with pGX6006 were comparable to pGX1421 in combination with pGX6006 (PD3: 609±597; PD4: 1636±999 SFU). There was not a significant difference between IFNγ ELISpot responses induced by pGX1411 in combination with pGX6006 and pGX1421 in combination with pGX6006 at any time point during the study (FIG. 18C). Further characterization by flow cytometry showed a trend toward more robust CD4+ T-cell responses with pGX1411 in combination with pGX6006 compared to pGX1421 in combination with pGX6006 two weeks PD4 (FIG. 19A). The phenotype and magnitude of responses in the CD8+ T-cell compartment were comparable for pGX1411 in combination with pGX6006 and pGX1421 in combination with pGX6006 (FIGS. 19B and 19C).

In summary, cellular immune responses directed at PRAME were comparable for the pGX1411 in combination with pGX6006 and pGX1421 in combination with pGX6006. Inclusion of IL-12 encoded by pGX6006 significantly increased cellular immune responses induced by pGX1421.

The nucleotide sequence (SEQ ID NO. 1) and amino acid (SEQ ID NO. 2) for synthetic consensus Prame are presented in Table 6 and Table 7, respectively.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modification to the disclosed embodiments, including without limitation those relating to the chemical structures, substituents, derivatives, intermediates, syntheses, compositions, formulations, or methods of use of the invention, may be made without departing from the spirit and scope thereof.

TABLE 6

Synthetic Consensus PRAME DNA Coding Sequence pGX1421

| SEQ ID NO. | SEQUENCE |
|---|---|
| 1 | atggactgga catggattct gttcctggtc gctgctgcta cacgggtgca ttcagagaga<br>cgaagactgc gggctcaat tcagagtagg tacatcagta tgtcagtctg gacctcacca<br>cggagactgg tggaactggc cgggcagagc ctgctgaagg atgaggccct ggctattgcc<br>gctctggaac tgctgccccg agagctgttc cctcccctgt tcatggcagc cttcgacgga<br>cgccacagcc agactctgaa ggctatggtc caggcatggc ccttttacctg cctgcctctg<br>ggcgtgctga tgaaggggca gcagctgcat ctggagactt tcaaagcagt gctggatggc<br>ctggacgtgc tgctgggcca ggaagtgagg cctaggcgct ggaagctgga ggtcctggat<br>ctgcgcaaaa acagccacca ggactttagg accgtgtggt ccgggaatcg ggccagtctg tactcattcc<br>cagaacccga ggctgcacag ccaatgcgga agaaaagaaa ggtggatgga ctgtccaccg aagctgagca<br>gcctttttaca ccaatcgaag tgctggtcga tctgtccctg aaagaaggcg catgcgacga gctgttctct<br>tatctgatgg agaaggtcaa aagacagaag aacgtgctgc acctgtgctg taagaaactg aaaatctttg<br>ctatgcccat gcaggacatc aagatgattc tgaaaatggt ccagctggat tccattgaag acctggaggt<br>cacttgtacc tggaagctgc caacactggc caaattctct ccctacctgg gacagatgat caatctgcga<br>cggctgctgc tgtctcacat ccatgctgac tcctctatta gtcctgagaa ggaggaagag tacattgcac<br>agtttactt tcagttcctg agtctgcagt gcctgcagge cctgtatgtg gatagcctgt tctttctgag<br>aggcaggctg accagctgc tgcgacacgt catgaacccc tggaaacac tgagtgtgac taattgtaga<br>ctgtcagagg gcgatgtgat gcatctgagc cagtccccta acgtgagcca gctgtccgtc ctgtctctga<br>gtggcgtgat gctgacagac gtgagccctg aaccactgca ggcctgctg gagcgagcat ctgccactct<br>gcaggacctg gattttgacg agtgtgggat catggacgat cagctgctgg tgctgctgcc ttcactgagc<br>cactgctccc agctgaccac actgtctttc tgtgggaacc caatctccat ttctgtgctg cagaatctgc<br>tgcaccatct gattggactg agcaacctga cccatgtgct gtacccccgtc cctctggaaa gctatgagga<br>tgtgcacgga acactgcatc tgggcaggct ggcctatctg cacgctcgcc tgcgagaagt ggtgtgcgag<br>ctgggcagac cctcaatggt gtggctgagc gccaatccat gtccccattg cggcgaccgg acattctacg<br>acccccgaacc tattctgtgc cctgcttca tgcctaactg ataa |

| TABLE 7 | | TABLE 7-continued | |
|---|---|---|---|
| Synthetic Consensus PRAME Protein Sequence pGX1421 | | Synthetic Consensus PRAME Protein Sequence pGX1421 | |
| SEQ ID NO. | SEQUENCE | SEQ ID NO. | SEQUENCE |
| 2 | MDWTWILFLVAAATRVHSERRRLRGSIQSRYISMSVW<br>TSPRRLVELAGQSLLKDEALAIAALELLPRELFPPLF<br>MAAFDGRHSQTLKAMVQAWPFTCLPLGVLMKGQQLHL<br>ETFKAVLDGLDVLLAQEVRPRRWKLEVLDLRKNSHQD<br>FWTVWSGNRASLYSFPEPEAAQPMRKKRKVDGLSTEA<br>EQPFTPIEVLVDLSLKEGACDELFSYLMEKVKRQKNV<br>LHLCCKKLKIFAMPMQDIKMILKMVQLDSIEDLEVTC<br>TWKLPTLAKFSPYLGQMINLRRLLLSHIHASSSISPE | | KEEEYIAQFTSQFLSLQCLQALYVDSLFFLRGRLDQL<br>LRHVMNPLETLSVTNCRLSEGDVMHLSQSPNVSQLSV<br>LSLSGVMLTDVSPEPLQALLERASATLQDLDFDECGI<br>MDDQLLVLLPSLSHCSQLTTLSFCGNPISISVLQNLL<br>HHLIGLSNLTHVLYPVPLESYEDVHGTLHLGRLAYLH<br>ARLREVVCELGRPSMVWLSANPCPHCGDRTFYDPEPI<br>LCPCFMPN |

What is claimed is:

1. A nucleic acid molecule comprising one or more nucleic acid sequences selected from the group consisting of:
   (a) SEQ ID NO: 1; and
   (b) a nucleic acid that is at least 96% identical to SEQ ID NO: 1, wherein the nucleic acid encodes a valine at amino acid position 487 and a valine at amino acid position 488 relative to SEQ ID NO: 2.

2. A nucleic acid molecule comprising one or more nucleic acid sequences selected from the group consisting of:
   (a) nucleotides 55 to 1584 of SEQ ID NO: 1; and
   (b) a nucleic acid that is at least 96% identical to nucleotides 55 to 1584 of SEQ ID NO: 1, wherein the nucleic acid encodes a valine at amino acid position 487 and a valine at amino acid position 488 relative to SEQ ID NO: 2.

3. A nucleic acid molecule comprising one or more nucleic acid sequences selected from the group consisting of:
   (a) a nucleic acid sequence that encodes SEQ ID NO: 2; and
   (b) a nucleic acid sequence that encodes a protein that is at least 96% identical to SEQ ID NO: 2, wherein the protein comprises a valine at amino acid position 487 and a valine at amino acid position 488 relative to SEQ ID NO: 2.

4. A nucleic acid molecule comprising one or more nucleic acid sequences selected from the group consisting of:
   (a) a nucleic acid sequence that encodes amino acids 19 to 526 of SEQ ID NO: 2; and
   (b) a nucleic acid sequence that encodes a protein that is at least 96% identical to amino acids 19 to 526 of SEQ ID NO: 2, wherein the protein comprises a valine at amino acid position 487 and a valine at amino acid position 488 relative to SEQ ID NO: 2.

5. A vector comprising the nucleic acid molecule of claim 1.

6. The vector of claim 5, wherein the vector is a plasmid or viral vector.

7. A composition comprising the nucleic acid molecule of claim 1.

8. A composition comprising the vector of claim 5.

9. A vaccine comprising the nucleic acid molecule of claim 1.

10. A vaccine comprising the nucleic acid molecule of claim 2.

11. The vaccine of claim 9 further comprising a pharmaceutically acceptable excipient.

12. The vaccine of claim 9 further comprising an adjuvant.

13. The vaccine of claim 12, wherein the adjuvant is IL-12, IL-15, IL-28, or RANTES.

14. A vaccine comprising the vector of claim 5.

15. A vaccine comprising:
(a) a nucleic acid molecule that encodes SEQ ID NO: 2;
(b) a nucleic acid molecule that encodes an antigen that is at least 96% identical to SEQ ID NO: 2, wherein the antigen comprises a valine at amino acid position 487 and a valine at amino acid position 488 relative to SEQ ID NO: 2;
(c) a nucleic acid molecule that encodes amino acids 19 to 526 of SEQ ID NO: 2; or
(d) a nucleic acid molecule that encodes an antigen that is at least 96% identical to amino acids 19 to 526 of SEQ ID NO: 2, wherein the antigen comprises a valine at amino acid position 487 and a valine at amino acid position 488 relative to SEQ ID NO: 2.

16. A vaccine comprising:
(a) a nucleic acid molecule comprising SEQ ID NO: 1;
(b) a nucleic acid molecule that is at least 96% identical to SEQ ID NO: 1, wherein the nucleic acid encodes a valine at amino acid position 487 and a valine at amino acid position 488 relative to SEQ ID NO: 2;
(c) a nucleic acid molecule comprising nucleotides 55 to 1584 of SEQ ID NO: 1;
(d) a nucleic acid molecule that is at least 96% identical to nucleotides 55 to 1584 of SEQ ID NO: 1, wherein the nucleic acid encodes a valine at amino acid position 487 and a valine at amino acid position 488 relative to SEQ ID NO: 2.

17. The vaccine of claim 15, further comprising a pharmaceutically acceptable excipient.

18. The vaccine of claim 15, further comprising an adjuvant.

19. The vaccine of claim 18, wherein the adjuvant is IL-12, IL-15, IL-28, or RANTES.

* * * * *